United States Patent
Cohen et al.

(10) Patent No.: US 12,213,733 B2
(45) Date of Patent: Feb. 4, 2025

(54) SYSTEM AND METHOD FOR DETECTING PHYSICAL CHARACTERISTICS OF A MULTILAYERED TISSUE OF A SUBJECT

(71) Applicant: ADOM, ADVANCED OPTICAL TECHNOLOGIES LTD., Lod (IL)

(72) Inventors: Yoel Cohen, Nes Ziona (IL); Ra'anan Gefen, Modiin-Macabim-Reut (IL); Yoel Arieli, Jerusalem (IL); Lee Barnea Nehoshtan, Ramat Hasharon (IL); Naor Deri, Kiryat Bialik (IL)

(73) Assignee: ADOM, ADVANCED OPTICAL TECHNOLOGIES LTD., Lod (IL)

( * ) Notice: Subject to any disclaimer, the term of this patent is extended or adjusted under 35 U.S.C. 154(b) by 191 days.

(21) Appl. No.: 17/921,438

(22) PCT Filed: Apr. 25, 2021

(86) PCT No.: PCT/IL2021/050472
§ 371 (c)(1),
(2) Date: Oct. 26, 2022

(87) PCT Pub. No.: WO2021/220266
PCT Pub. Date: Nov. 4, 2021

(65) Prior Publication Data
US 2023/0157535 A1    May 25, 2023

(30) Foreign Application Priority Data
Apr. 27, 2020    (IL) .......................................... 274295

(51) Int. Cl.
*A61B 3/10*    (2006.01)
*A61B 3/00*    (2006.01)

(52) U.S. Cl.
CPC ............ *A61B 3/101* (2013.01); *A61B 3/0025* (2013.01); *A61B 3/0083* (2013.01); *A61B 3/0091* (2013.01)

(58) Field of Classification Search
CPC ..... A61B 3/101; A61B 3/0025; A61B 3/0083; A61B 3/0091; A61B 3/10; A61B 5/0066; A61B 5/1075; A61B 5/0075; A61B 3/152
See application file for complete search history.

(56) References Cited

U.S. PATENT DOCUMENTS

| | | | |
|---|---|---|---|
| 2007/0255169 A1* | 11/2007 | Hashimshony | A61B 5/415 606/1 |
| 2010/0160754 A1* | 6/2010 | Durkin | A61B 5/0086 600/342 |

(Continued)

FOREIGN PATENT DOCUMENTS

| | | |
|---|---|---|
| WO | 2015132788 | 9/2015 |
| WO | 2019232575 | 12/2019 |

OTHER PUBLICATIONS

Lu Hui et al: "Tear film measurement by optical reflectometry technique", Journal of Biomedical Optics, SPIE, 1000 20th St. Bellingham WA 98225-6705 USA, vol. 19, No. 2, Feb. 1, 2014 (Feb. 1, 2014), p. 27001.

(Continued)

*Primary Examiner* — Hien N Nguyen
(74) *Attorney, Agent, or Firm* — Niels Haun; Dann, Dorfman, Herrell & Skillman, P.C.

(57) ABSTRACT

Systems and methods for detecting physical characteristics of a multilayered tissue of a subject, such as a tear film including analyzing received detector-output indicative of optical properties of light reflected or deflected from the respective multilayered tissue, to determine spectral properties of the multilayered tissue; and determining physical characteristics of the multilayered tissue by using multiple (Continued)

spectral models of the of the multilayered tissue, each model being associated with spectral properties indicative of different tissue characteristics, wherein physical characteristics of the multilayered tissue are determined by hierarchal determination of a best-fit model from the multiple spectral models.

16 Claims, 12 Drawing Sheets

(56) References Cited

U.S. PATENT DOCUMENTS

| | | | |
|---|---|---|---|
| 2011/0206291 | A1 | 8/2011 | Kashani |
| 2013/0293842 | A1 | 11/2013 | Grenon |
| 2014/0152958 | A1 | 6/2014 | Okamoto |
| 2014/0285767 | A1 | 9/2014 | Korb |
| 2016/0338585 | A1 | 11/2016 | Arieli |
| 2017/0061621 | A1* | 3/2017 | Wortman .............. G06T 7/0016 |
| 2019/0183333 | A1* | 6/2019 | Arieli ................... A61B 3/1005 |
| 2019/0231187 | A1 | 8/2019 | Wang |
| 2019/0290120 | A1 | 9/2019 | Salkola |
| 2020/0383564 | A1* | 12/2020 | Millar .................. A61B 5/4848 |
| 2022/0034716 | A1 | 2/2022 | Cohen |
| 2022/0313077 | A1* | 10/2022 | Singh ...................... A61B 3/14 |

OTHER PUBLICATIONS

International Search Report and Written opinion dated Jul. 23, 2021 from PCT/IL2021/050472.

"Line edge roughness detection using deep UV light scatterometry." Barak Yaakobovitz, Yoel Cohen, Yoed Tsur, Microelectronic Engineering, vol. 84, Issue 4, Apr. 2007, pp. 619-625 (2006).

"Tear film imager for dynamic mapping of the human tear film." Yoel Cohen, Shlomi Epshtein, Alon Harris, Raanan Gefen, Lawrence Kagemann, and Yoel Arieli; Applied Optics, vol. 58, Issue 29, pp. 7987-7995 (2019).

"Application of novel Interferometric method to investigate the relation between lipid layer thickness and tear film thinning." P.E. King-Smith, E.A. Hinel, J.J.Nichols, Invest Ophtalmol. Vis. Sci 51, No. 5 (2010) 2418-2423.

"A compositional based model for the tear film lipid layer," J.P. McCulley, W. Shine; Trans. Am. Ophthalmol. Soc. 95 (1997) 79-88 discussion 88-93.

"Computer-Assisted Calculation of the exposed area on the human eye" J.M. Tiffany, B.S. Todd, M.R. Baker, Nuffield Laboratory of Ophthalmology Computing Laboratory, and Visual Sciences Unit University of Oxford Oxford, United Kingdom(1998) 433-436 & 439.

"Dynamic assessment of the tear film muco-aqueous and lipid layers using a novel tear film imager (TFI)," Segev F, Geffen N, Galer A, et al., British Journal of Ophthalmology 2019; pp. 1-6.

"Tear film lipid layer: A molecular level view." Lukasz Cwikilik, Biochimica et Biophysica Acta 1858 (2016) 2421-2430.

"Dry eye disease caused by viral infection: review," Monica Alves, Rodrigo Nogueira Angerami, Eduardo Melani Rocha. Arq Bras Oftalmol. 2013;76(2):129-32.

* cited by examiner

SYSTEM AND METHOD FOR DETECTING PHYSICAL CHARACTERISTICS OF A MULTILAYERED TISSUE OF A SUBJECT

RELATED APPLICATIONS

This application is a national stage application under 35 U.S.C. 371 for International Application No. PCT/IL2021/050472, which claims the priority of Israel Application No. 274295, filed on Apr. 27, 2020, the entire contents of which application are incorporated herein by reference.

FIELD OF EMBODIMENTS OF THE INVENTION

The present application relates to detection of characteristics of multilayered tissues, and more specifically to optical detection of multilayered tissues characteristics.

BACKGROUND

Traditional imaging methods are unable to accurately detect the depth of the semitransparent biological multilayered tissues. Such methods fail to diagnose thin underlayers and very small structures. In recent years, to overcome this limitation, the emerging method is to use OCT (optical coherence tomography). However, such methods are limited in several ways, including in the following ways:

(1) The basic axial resolution that such methods provide are only suitable for layers that are of tens of microns.

(2) Most OCT methods require a scanning mode, which creates a limitation regarding the time intervals at which data can be acquired or alternatively has a signal to noise tradeoff and limitations in measurement of fast trends or moving objects. Such limitations are critical for the measurement of a very thin layers that undergo rapid dynamic changes (such as the tear film, which undergoes dynamic changes due to liquid flow).

(3) The need for higher signal to noise ratio enforces the use of a laser or a swept source that have disadvantages in terms of cost, wavelength bandwidth and safety requirements (e.g. high energy or large integration time that must be applied to measure a moving liquid flow with a maximal SNR).

(4) The extraction of a meaningful parameter is harder if the layers change in time or if the measurement is interrupted, for example by blinking or out of focus events.

For the above reasons, OCT measurements are not commonly used for thin layers that undergo dynamic changes (such as the tear film). Rather, a preferred method is to combine fast spectrometric data acquisition with camera frame grabbing for analysis and movement control.

Broadband spectral measurements are sensitive to the interferences of light waves reflected from interfaces and to the relative difference in their values at different wavelengths thus they can give high resolution and sensitivities of thicknesses of several nanometers.

Thin substances measured at high resolution enables differentiation of the fine changes in these layers or structures, even under changing dimensions and/or random fluctuations in their dimensions, as described in Barak Yaakobovitz et al., (2006).

The Tear film lipid layer thickness:

The tear film is an example of a multilayer tissue having very thin layers. The lipid layer of the tear film is a thin layer, which in some cases may contain an additional internal sub layer. The tear film additionally contains an aqueous layer, a mucus layer and microvilli, all of which are disposed beneath the lipid layer. The aqueous and mucus layers are sometimes jointly referred to as the mucu-aqueous layer.

Fine thickness measurement by advanced optical methods of the aqueous layer of the tear film is required for understanding the tear film stability, which is a root causes for dry eye syndrome, and therefore has importance. Non stability attributed to the dry eye phenomena may be affected by the upper lipid layer of the tear film. The homeostasis of this layer is important for the health of the tear film since it is the protective cover for the mucuaqueous and lower layers. Beside the prevention of fast evaporation and smoothing the surface, the lipid layer has a role for surface tension reduction, as described in Lukasz Cwikilik, (2016). The thickness of the lipid layer in the tear film was estimated by recent interferometric measurements to 15 nm-160 nm with a mean of 42 nm P. E. King-Smith et al., (2010). It is understood in the field of tear-film analysis that the tear film lipid layer has a complex composition and is organized in a multilayered fashion. A commonly-accepted view assumes that the interface between the lipid layer and the underlying aqueous layer is formed by a thin sublayer of a polar amphiphilic lipid and topped by a relatively bulky layer of non-polar hydrophobic lipids occupying the outermost eye-air interface. J. P. McCulley et al., (1997), and J. M. Tiffany et al., (1997). An alternative viewpoint is that that the lipid layer may be considered as a single layer, this viewpoint being presented, for example, in Segev F, et al., (2019).

Liquid tissues, such as the tear film, that are disposed at the front of the eye and therefore act as an interface with the outside environment, may be somewhat impacted by the ambient environment. There is evidence that the tear film may become infected with viruses and other small cells, as presented, for example, in Monica Alves et al., (2013).

SUMMARY OF EMBODIMENTS

Aspects of disclosed embodiments pertain to a system for detecting physical characteristics of a multilayered tissue of a subject, the system comprising:
  an optical subsystem comprising at least:
  a broadband light source configured and positioned to directly or indirectly illuminate the multilayered tissue; and
  at least one optical detector, configured and positioned to optically detect one or more optical properties of the multilayered tissue; and
  a processing module operatively associated with the optical subsystem, the processing module being configured to: (i) receive detector-output from the at least one optical detector; (ii) determine spectral properties of the multilayered tissue by processing the received detector-output; and (iii) determine physical characteristics of the multilayered tissue by using multiple spectral models of the of the multilayered tissue comprising at least: a first model assuming a normal condition of the multilayered tissue and one or more additional models, assuming abnormal conditions of the multilayered tissue, each model being associated with different spectral properties, wherein physical characteristics of the multilayered tissue are determined by hierarchal determination of a best-fit model from the multiple spectral models, based on determination of best-fit of the multilayered tissue to one of the spectral model.

Additional or alternative aspects of disclosed embodiments pertain to a method for detecting physical characteristics of a multilayered tissue of a subject, the method comprising at least the steps of:

receiving detector-output from at least one optical detector, the detector-output being indicative of optical properties of light reflected or deflected from the respective multilayered tissue;

analyzing the received detector-output to determine spectral properties of the multilayered tissue; and determining physical characteristics of the multilayered tissue by using multiple spectral models of the of the multilayered tissue comprising at least: a first model assuming a normal condition of the multilayered tissue and one or more additional models, assuming abnormal conditions of the multilayered tissue, each model being associated with different spectral properties of the multilayered tissue, wherein physical characteristics of the multilayered tissue are determined by hierarchal determination of a best-fit model from the multiple spectral models, based on determination of best-fit of the multilayered tissue to one of the spectral models.

Additional or alternative aspects of disclosed embodiments pertain to a method for detecting physical characteristics of a multilayered tissue of a subject, the method comprising at least the steps of:

irradiating a multilayered tissue using at least one light sources;

detecting optical properties of light reflected or deflected from the respective multilayered tissue, using at least one optical detector outputting detector-output, the optical properties of the tissue comprising at least polarization of light reflected or deflected from the multilayered tissue; and determining physical characteristics of the multilayered tissue, based on the optical properties thereof.

BRIEF DESCRIPTION OF THE DRAWINGS

FIG. 2A illustrates layers of a normal tear film and FIG. 2B illustrates an abnormal tear film layers in which the lipid layer is separated by an intermediate aqueous layer;

FIG. 10A shows a raw image of an eye with two grids indicated over the raw eye image, and FIG. 10B shows an image of a lipid layer thickness map disposed over the eye image such as to show thicknesses of the lipoid layers over their corresponding locations in the cornea surface, the lipid layer thickness map having been generated based upon the color intensity ratios of the reflected light from respective locations of the cornea of the eye, in accordance with some applications of the present invention;

DETAILED DESCRIPTION OF EMBODIMENTS

Figure 1:
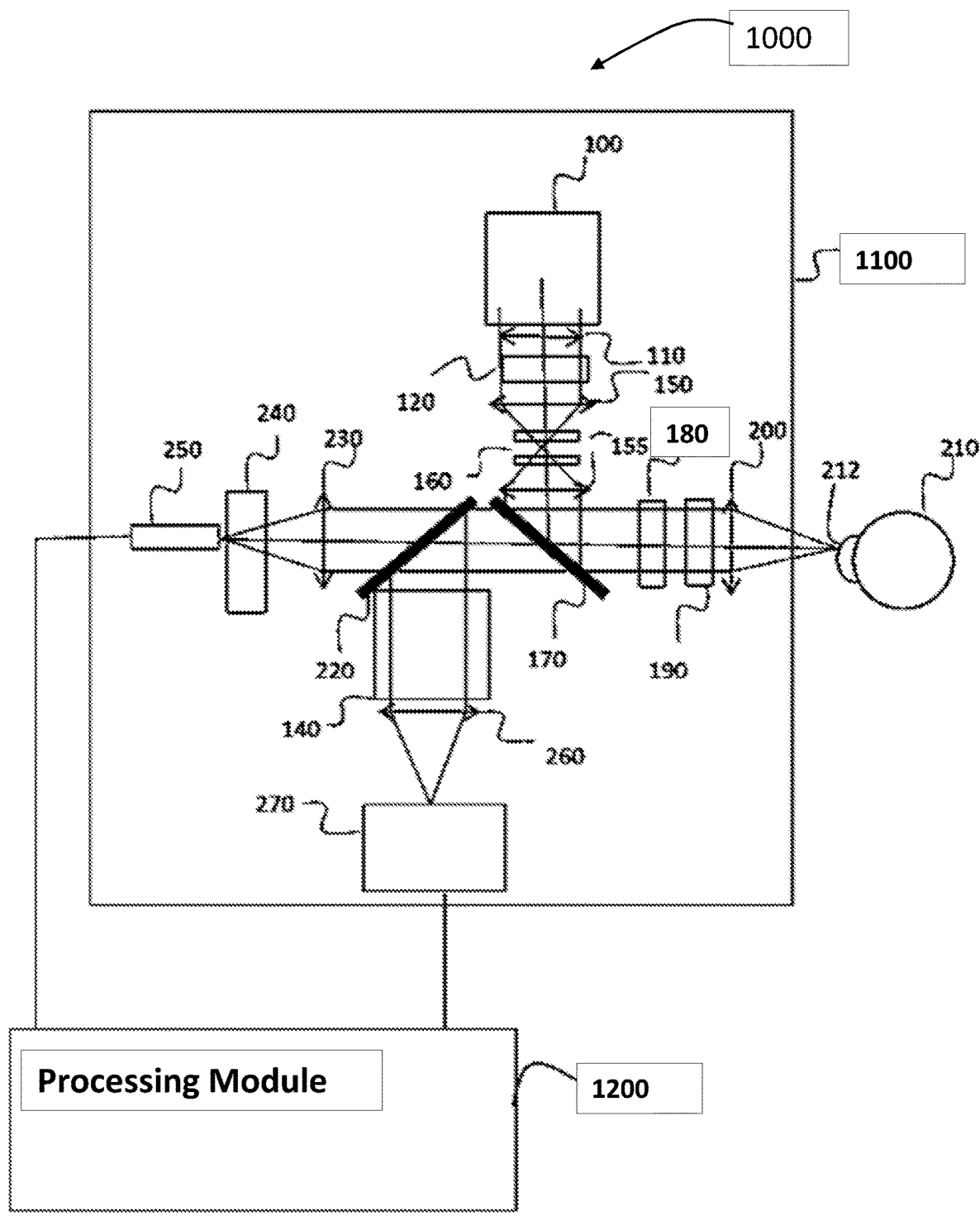
FIG. 1 is a schematic illustration of an optical system and a computer processor that is configured to analyze measurements that are performed by the optical system using algorithms that are in accordance with some applications of the present invention.

Aspects of disclosed embodiments pertain to systems and methods for determining physical characteristics of a multilayered tissue such as, yet not limited to, the tear film of an eye if a subject, by obtainment of spectral properties of the tissue (e.g, by measuring and/or calculating based on detected data) as can be seen in Yoel Cohen et al., (2019).

The terms "multilayered tissue", "multilayer tissue" and/or "tissue" may be used herein interchangeably.

Aspects of disclosed embodiments pertain to a system for detecting physical characteristics of a multilayered tissue of a subject, the system comprising:

an optical subsystem comprising at least: a broadband light source configured to directly or indirectly illuminate the multilayered tissue; and at least one optical detector, each configured and positioned to optically detect one or more optical properties of at least one area and/or layer of the multilayered tissue; and a processing module operatively associated with each of the at least one optical detector, the processing module being configured to:

receive detector-output of each of the at least one optical detector, indicative of optical properties of light reflected or deflected from the respective multilayered tissue;

analyze the received detector-output to determine spectral properties of at least one layer of a specific layer-type of the multilayered tissue; and for at least one of the layers of at least one layer-type of the multilayered tissue, determine a best-fit model from plurality of spectral models of the respective at least one layer-type, for representing different physical characteristics of the respective layer of the respective layers-type, the determination of the best-fit model being done based on determination of best-fit of spectral properties of the model to the determined spectral properties of the corresponding one or more layers of the multilayered tissue; and determine physical characteristics of the respective layer of the multilayered tissue, based on the determined best-fit model.

Other aspects of disclosed embodiments, pertain to a method for detecting physical characteristics of a multilayered tissue of a subject, the method comprising at least the steps of:

receiving detector-output from at least one optical detector, the detector-output being indicative of optical properties of light reflected or deflected from the respective multilayered tissue;

analyzing the received detector-output to determine spectral properties of at least one layer of a specific layer-type of the multilayered tissue; and for at least one of the layer-types of the multilayered tissue: determining a best-fit model from plurality of spectral models of the respective layer-type, for representing different physical characteristics of the respective layer of the respective layer-type, the determination of the best-fit model being done based on determination of best-fit of spectral properties of the model to the determined spectral properties of the corresponding layer of the multilayered tissue; and determining physical characteristics of the respective layer of the multilayered tissue, based on the determined best-fit model.

Additional aspects of disclosed embodiments pertain to a method for detecting physical characteristics of a multilayered tissue of a subject, the method comprising at least the steps of:

irradiating a multilayered tissue using at least one light sources;

detecting optical properties of light reflected or deflected from the respective multilayered tissue, using at least one optical detector outputting detector-output, the optical properties of the tissue comprising at least polarization of light reflected or deflected from the multilayered tissue; and determining physical characteristics of the multilayered tissue, based on the optical properties thereof.

The identification of polarization of the reflected or deflected light may optionally be done by using at least one polarizer and a mechanism that is configured for changing the polarization over time (e.g. rotatable polarizing element) of light emanating from the light source or reflected/deflected from the multilayered tissue.

It is noted that the terms "spectral model" and "model" may be used interchangeably in this document.

Reference is now made to FIG. 1, which is a schematic illustration of a system 1000 for determining physicals characteristics of a multilayered tissue by detecting optical (spectral) properties of the multilayered tissue and comparing spectral behavior of the detected spectral characteristics of the tissue, an area or a layer thereof, with known spectral behavior of the same tissue, area or layer thereof, in different known states of the corresponding tissue/area/layer (defining physical characteristics of that tissue/area/layer). The system 1000 shown in FIG. 1 is generally similar to optical systems described in U.S. Pat. No. 9,757,027 (B2) to Arieli Yoel et al., which is incorporated herein by reference in its entirety.

The system may be used for optically measuring characteristics of a biological tissue or a biological substance such as the lipid and the aqueous layers of a cornea 212 of an eye 210 over a large area. The measurements may be analyzed using algorithms that are operated by processing module 1200, the algorithms being as described herein.

For some applications, optical system includes a combination of a spectrometer 250 and/or an interferometer 140 and a color camera 270. The contrast of the spectral oscillations originated from the aqueous layer interference is always considerably less than the contrast that can be obtained from the lipid layer. This fact is due to the anti-reflection coating effect caused by the mucus layer under the aqueous layer on the cornea, as well as microvilli scattering. However, this effect is much stronger in the visible range of the spectrum (400-800 nm) than in the near IR.

This effect can be overcome by combining (a) a spectrometer and/or an interferometer in the near infrared and visible region (NIR-VIS) and (b) a color camera. The spectrometer and/or camera provides the information of the interference in the NIR and the VIS. From the information of the interference in the NIR obtained by the interferometer and/or the spectrometer, the thickness of the aqueous layer is calculated. From the information of the color contrast (sub section of a fringe) in the VIS by the camera, the thickness of the lipid layer is calculated. The accurate color of the point(s) where the spectrometer measures, can be calculated and the result can be used for calibrating the camera.

According to some embodiments, light passes along two paths; an illumination path and an imaging path. For some applications, along the illumination path, the light is generated by a broadband light source 100, is collimated by lenses 110 and (optionally) filtered by a filter 120. The optional interferometer can be disposed in the illumination path or alternatively in the imaging path (to be described below). The light is focused by a lens 150 on at least two grids 160 and collimated by a lens 155. Grids 160 may be imaged on the object to be measured, e.g., cornea 212 of eye 210. For some applications, grids 160 are used for autofocusing and positioning the cornea at a predetermined distance from components of the system by examining the sharpness of the images of the grids on the cornea. In cases of normal incidence, the light passes through beam-splitter 170.

For some applications, autofocusing is performed directly on the image of features that exists on the cornea (e.g. lipids topography or simply the iris). The light is directed to the cornea by a focusing optical element (e.g., a lens) 200. The focusing optical element 200 may be any kind of focusing optical element such as a compound lens, a Fresnel lens, Diffractive Optical element, etc. The light is focused to the approximated focal point of the concave mirror formed by the corneal surface such that it is reflected back at a small angle relative to the optical axis. The reflected light is gathered by the central part of the focusing optical element 200 or by an additional optical element placed in the central part of the focusing optical element 200. Optionally, other optical elements 180 may be disposed along one or both of the light paths, such as a polarizer, which can contribute to proper background removal. For some applications, the optical element 180 is a narrow aperture optical element. For some applications, the optical element is a variable aperture, e.g., as described hereinbelow with reference to Case 2. A reticle 190 may also be disposed along one of the light paths to serve as a target for directing the subject's gaze. In the imaging path, the light reflected from the cornea is partially reflected by the beam splitter 220 and focused on the camera 270, by lens 260, to image the cornea. The transmitted light through the beam splitter 220 is focused on the spectrometer 250, using the lens 230, and is analyzed by processing module 1200.

In order to increase the accuracy of the autofocusing and/or to center the measured cornea relative to the optical axes of the camera and/or the spectrometer, a known pattern such as a circle or a square or some other structured light pattern may be projected onto the cornea using a projector. Due to its curvature, when the cornea is decentered relative to the optical axis, the image of the projected pattern is distorted. For some applications, this distortion is processed and used to center the cornea in real time.

As mentioned above, the spectral information of the interference in the NIR provided by the spectrometer and/or interferometer may be used for calculating the thickness of the aqueous layer, and the information of the color contrast in the VIS provided by the camera may be used for calculating the thickness of the lipid layer. In addition, for some applications, the information of the reflectance contrast per wavelength provided by the interferometer and/or the spectrometer in the VIS is used for calibrating the color camera, e.g., as described in U.S. Pat. No. 9,757,027 to Arieli, which is incorporated herein by reference.

For some applications, the combined VIS-NIR spectrum can be analyzed using 3D electromagnetic simulation known in the art such as FTDT (Finite-Difference Time-Domain) or RCWT (Rigorous Coupled Wave Theory) or Green Function based calculations. The measured reflection of light from the cornea can be compared iteratively to a simulated reflectance from a simulated cornea until a final fit is achieved for best corneal structure parameters. In this manner, any combination of the thicknesses of the lipid layer, aqueous layer, mucin layer and microvilli roughness are calculated simultaneously.

For some applications, when the interferometer 140 is disposed in the imaging path before the camera 270, the optical path difference (OPD) between the interferometer's mirrors is increased, such that an interferogram is obtained for each point of the camera image. For some applications, the Fourier transform of the interferogram is obtained at each point of the image provides, such as to provide a spectrum at that point. The spectrum may be analyzed for calculating the thickness of the lipid and aqueous layers at each point of the image. Since the spectrum in at least one point of the image is obtained also by the spectrometer, the spectrum obtained by the spectrometer and the colors obtained by the camera are compared and the movements of the interferometer's mirrors may be calibrated accordingly.

For some applications, interferometer 140 is disposed within the illumination path, as an alternative or in addition to being disposed within the imaging path. For some such applications, the light from the light source is modulated by a cosine function as a function of the OPD between the interferometer's mirrors. A Fourier transform of the intensity of light at each point of the image as a function of the OPD may be obtained, in order to provide the light spectrum. The light spectrum may be analyzed for calculating the thickness of the lipid and aqueous layers. Since the spectrum of at least one point of the image is also obtained by the spectrometer, the spectra obtained by the spectrometer and the spectrum obtained by the interferometer are typically compared and the movements of the interferometer's mirrors are calibrated accordingly.

The calibration of the response of the color camera using either the spectrometer, the interferometer or both, may be critical for lipid-layer measurements where the sensitivity of the color change as a function of the lipid layer thickness may be relatively high, especially at the shorter wavelengths.

For some applications, in order to increase the number of the points of the spectrometer's measurements, a deflecting element 240 is disposed along the imaging path of the spectrometer. The deflecting element 240 typically deflects the incoming light from the cornea in such a way that at each time the light from different points of the cornea is analyzed by the spectrometer. For some such applications, the calculations of the aqueous layer thickness are performed at several points and the calibration of the color camera is performed at several points of the image.

For some applications, additional optical elements 180 are added to one or both of the light paths, such as, a polarizer or a narrow aperture optical element, etc. The addition of a polarizer and/or a narrow aperture optical element may improve the signal, for example, by blocking non-specular reflected light, and/or by blocking light reflected by the layers under the cornea. (Such layers typically depolarize and rotate the polarization of illuminating light and/or are reflected in non-specular manner.) Typically, a polarizer is used to block light reflected from the iris of the eye.

For some applications, a narrow band filter is disposed between the light source and the camera. Typically, in such cases, the image has interference patterns in the form of fringes that are obtained by interfering light beams reflected from the different interfaces of the layers of the tear film. These layers may have thickness non-uniformities. The combination of non-uniformities of the layers thicknesses obtained from the interference patterns with the information obtained at specific discrete points from the accurate spectrometry measurements may be used to provide a continuous full image with absolute thickness values per pixel. For some applications, the above-described combination is used to overcome the ambiguity of the interference cycles.

It is noted that the term "spot size" as used herein in conjunction with spectrometric measurements should be interpreted as meaning the diameter of the area (i.e., a round area) of the detected object from which reflected light is received by the spectrometer in a given spectrometric measurement. When used herein in conjunction with an interferometric measurement, the term "spot size" should be interpreted as meaning the diameter of the area of the detected object corresponding to pixels that are binned together with each other in the interferometric measurement. As noted hereinabove, typically the interferometer is used together with an imaging camera, such as camera 270. The term "sampling size" may be used interchangeably with the term "spot size". For some applications, a single spot is sampled (e.g., a single spot at the center of the measurement area, such as the center of the tear film). For some applications, a plurality of spots may be sampled, e.g., more than two, and/or less than five (e.g., two to five spots) may be sampled.

In typical applications of the present invention, thickness and/or spectral measurements of a thin biological layer are performed using one or more measurement parameters described hereinbelow. Typically, measurements are performed on a thin biological layer in order to determine the thickness of the layer, and/or the changes over time of a parameter (such as, the thickness) of the layer. A thin biological layer typically may include one or more sub-layers. For example, the tear film typically includes tear film inner layers, such as the lipid and/or the aqueous layers, the mucus layer, microvilli, and/or one or more delicate membranes, such as the basement membrane and/or the inner limiting membrane. A thin biological layer as described herein may include the tear film and/or any one of the aforementioned constituent layers of the tear film. For some applications, such measurements are performed using the optical system described hereinabove with reference to FIG. 1. For some applications, a combination of two or more measurements is performed on the tear film, e.g., using techniques described hereinabove. For example, a high quality and high resolution spectral and/or interferometric measurement of a single spot (or a plurality of spots) may be performed, together with high quality and large field-11 of-view imaging of the reflection from a given inner layer of the tear film. For some applications, measurements as described herein are performed using a spectrometer, an optical camera, an interferometer, and/or a different imaging device, without using other components belonging to the optical system shown in FIG. 1. Measurements may be performed in order to determine clinical parameters that are indicative of the root cause of a dry eye diagnosis and/or the health of the tear film. For example, such parameters may include blink rate, tear break up time, variation of lipid thickness with time, lipid uniformity, aqueous layer thickness, evaporation rate, etc. For some applications, two or more of the following parameters are measured simultaneously: aqueous flow rate, aqueous layer thickness, lipid layer integrity, lipid layer sublayers and components, and evaporation rate. For some applications, such measurements by combining techniques described herein with techniques as described in U.S. Pat. No. 9,757,027(B2), which is incorporated herein by reference.

Figure 2A:
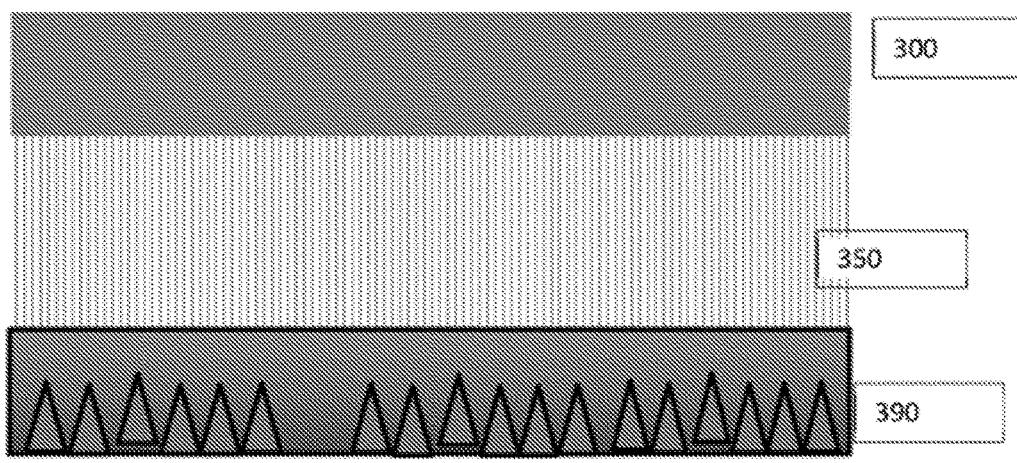
FIGS. 2A and 2B are schematic illustrations of, respectively, layers of a tear film of a normal eye, and layers of a tear film having an intermediate aqueous layer within the lipid layer that is detected in accordance with some applications of the present invention.
Figure 2B:
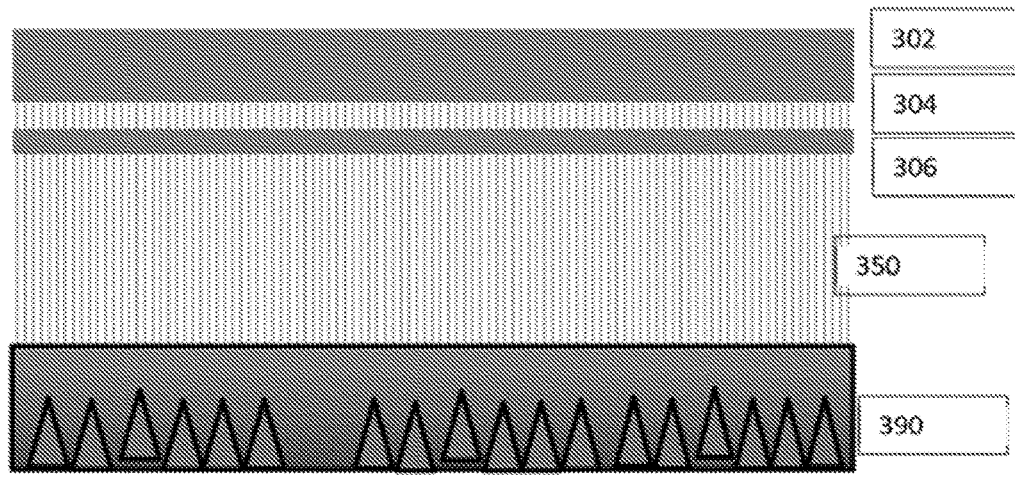

Reference is now made to FIG. 2A which is schematic illustration of layers of a tear film of a normal eye (herein associated with a "stack I" tear film configuration or state), the layers including a lipid layer 300, a mucu-aqueous layer 350, and a rough epithelium layer 390 (containing microvilli). Reference is also made to FIG. 2B, which is a schematic illustration of layers of a tear film having an upper lipid layer 302, a lower lipid layer 306, and an intermediate aqueous layer 304 disposed between the upper and lower lipid layers (herein associated with a "stack II" tear film configuration or state). For some applications of the present invention, parameters of the tear film are extracted by analyzing the measured parameters of the tear film using a combination of two interpretation steps. The first step is based on a model of the tear film shown schematically in FIG. 2A, which is the normal model for a healthy eye. The analysis of the measured parameters based upon the model of the eye shown in FIG. 2A, is performed by simulating the reflectance of a simulated tear film with starting conditions and comparing it to the measured reflectance from the spectrometer or interferometer and camera. For example, by performing a global minima search using an appropriate merit function, a best fit may be found in iterative mode. Typically, known mathematical methods are used such a Simplex, Steepest decent, stimulated annealing or Levenberg-Marquardt. For some applications, the processing module outputs the best fit result as the measurement result. It is noted that, as described in the Background section, the mucus and aqueous layers are sometimes described in literature as two separate layers, and they are sometimes jointly referred to as the mucu-aqueous layer. In practice, the mucus and aqueous layers are continuous with each other, with no distinct interface between the two layers. Since there is no distinct interface between these two layers, when optical reflectance measurements are being made, the mucus and aqueous layers typically cannot be clearly distinguished from each other. Therefore, the reflectance measurements that are performed in accordance with some applications of the present invention, may be performed such that there is no (or minimal) reflected light from the interface (if any) between the mucus and aqueous layers. Consequently, in the analysis of the tear film that is performed, the aqueous and mucus layers may be treated as single combined layer. For this reason, the mucu-aqueous layer is referred to herein as a single layer, with reference to some applications of the invention.

Figure 3:
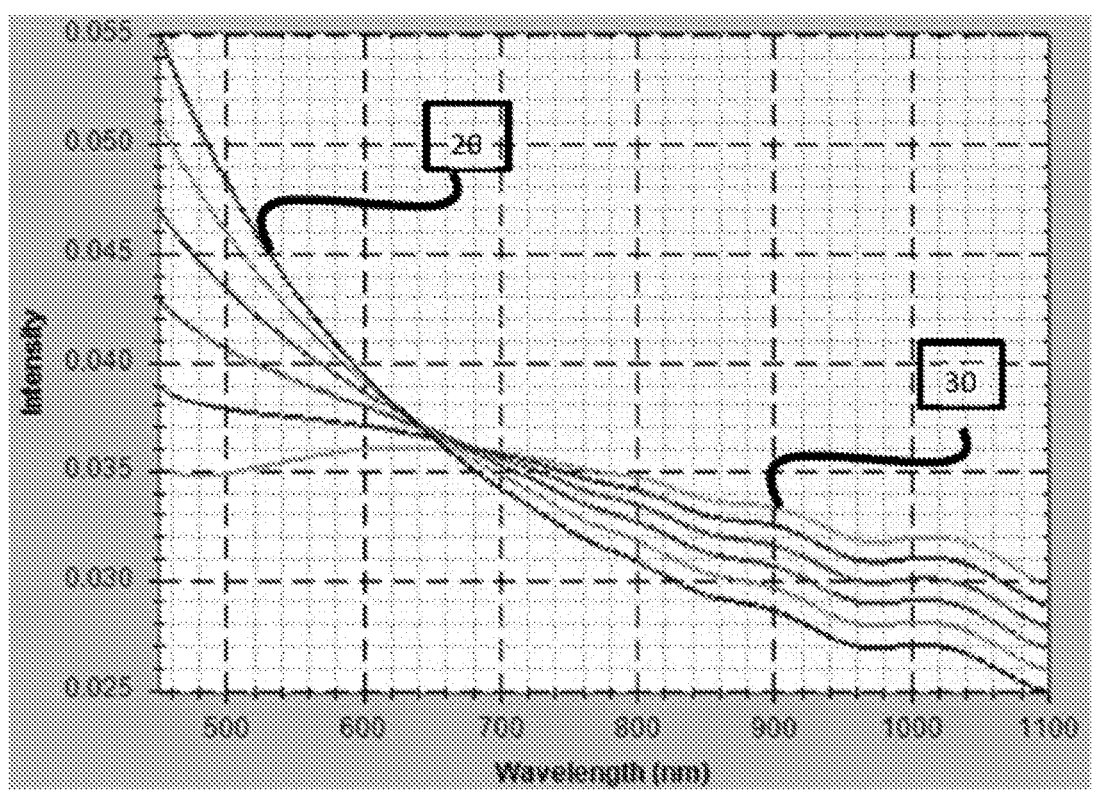
FIG. 3 is a graph showing reflectance versus wavelength for a tear film as shown in FIG. 2B, in which an intermediate aqueous layer of 50 nm is disposed within the lipid layer, respective curves of FIG. 3 corresponding to the lower lipid layer having respective thicknesses, in accordance with some applications of the present invention;.

The model of the tear film shown in FIG. 2B typically has a different spectral reflectance than the common model (shown in FIG. 2A). In this context, reference is now made to FIG. 3, which is a graph showing reflectance intensity versus wavelength for a tear film as shown in FIG. 2B, respective curves of FIG. 3 corresponding to the lower lipid layer having respective thicknesses. The graph shown in FIG. 3 shows the reflectance intensity from a tear film having a general structure as shown in FIG. 2B, and with mucu-aqueous layer 350 having a thickness of 2576 nm, rough epithelium layer 390 having a thickness of 2900 nm, upper lipid layer 302 having a thickness of 50 nm, intermediate aqueous layer 304 having a thickness of 50 nm. Respective curves of the graph correspond to lower lipid layer 306 having thicknesses of respectively 0 nm, 4 nm, 8 nm, 12, nm, 16 nm, and 20 nm.

Note that the case of 0 nm thickness (curve 20) essentially corresponds to the common tear-film model described in FIG. 2A. The reflectance corresponding to the lower lipid layer having a thickness of 20 nm is represented by curve 30. Curve 20 (corresponding to the common tear-film model) exhibits a negative slope, with higher reflectance at lower wavelengths. At lower wavelengths there are two differences between the two models, as may be demonstrated by contrasting curve 20 with curve 30:

(1) For the model shown in FIG. 2A (curve 20), the slope of the curve is always negative, whereas in some cases of the model shown in FIG. 2B (e.g., curve 30), the slope contains a non-negative portion (with this effect typically being exhibited when the lower lipid layer having a thickness of more than 12 nm)

(2) The absolute reflectance of the model shown in FIG. 2A may be substantially higher than for the model shown in FIG. 2B. (Note that an initial condition for the difference between the models is that the total lipid thickness is greater than 50 nm, otherwise the values of upper lipid layer 302, mucu-aqueous layer 304, and bottom lipid layer 306 are thin, such that the analysis is close to the resolution limits.)

Figure 4:
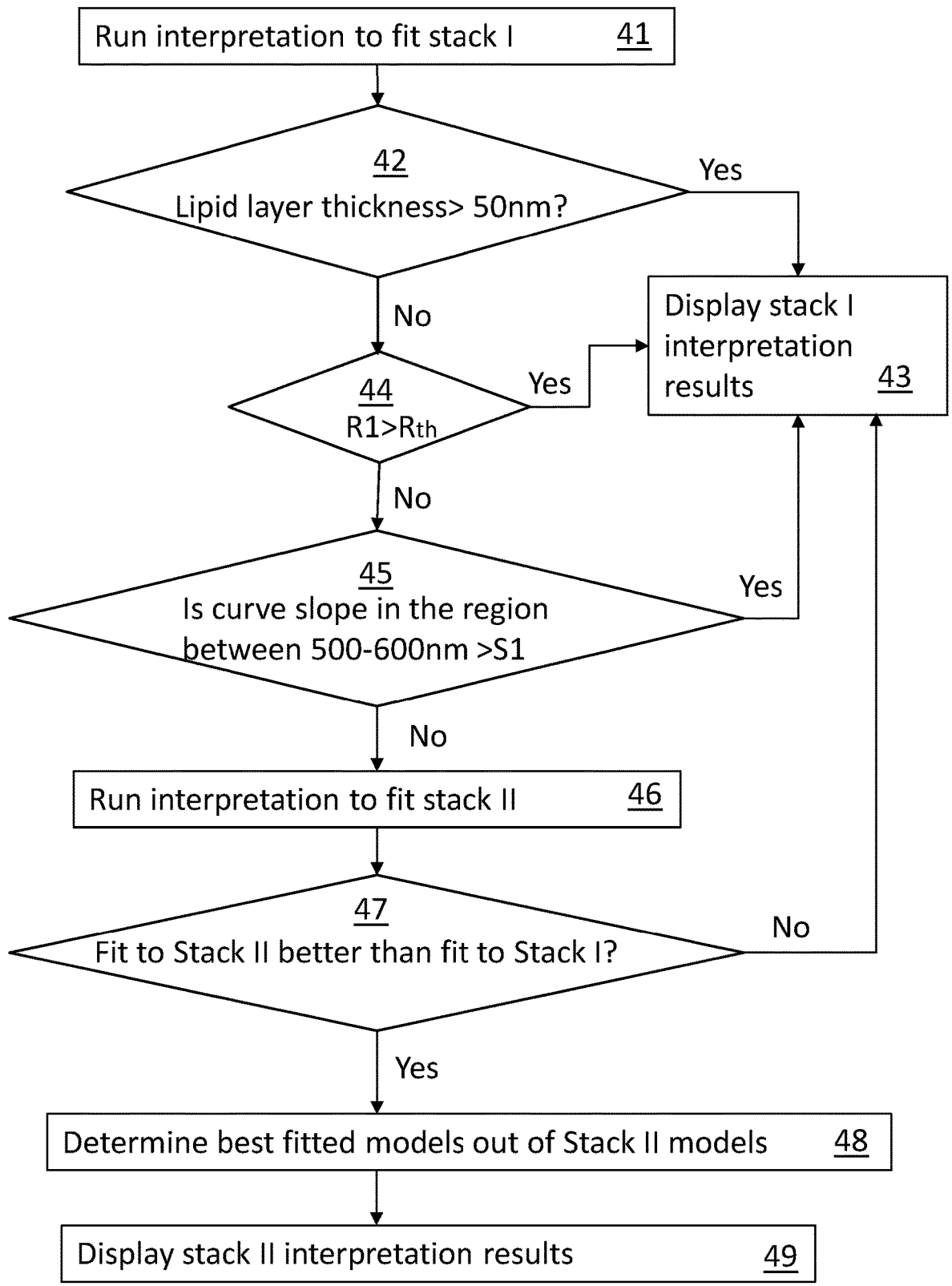
FIG. 4 is a flowchart showing steps of an algorithm that is performed upon a tear film, the algorithm including steps for determining whether the tear film best fits a model as shown in FIG. 2A or FIG. 2B, in accordance with some applications of the present invention.

FIG. 4 shows is a flowchart illustrating steps of an algorithm that is performed upon a tear film, the algorithm including steps for determining whether the tear film best fits a model as shown in FIG. 2A or as shown in FIG. 2B, in accordance with some embodiments. In some embodiments, the algorithm is performed by processing module 1200 (FIG. 1). It is noted that in the model shown in FIG. 2B, there are two extra parameters as compared to the model shown in FIG. 2A: the intermediate mucu-aqueous layer thickness and the bottom lipid layer thickness. Therefore, it is expected that if the tear film is in fact as shown in FIG. 2B, an analysis using this model will yield a better best fit result than is analyzed based on the model shown in FIG. 2A. Therefore, the analysis of the tear film may be performed using an algorithm as shown in FIG. 4, in accordance with which the processing module determines whether the best-fit model of tear film stack should be performed according to the model shown in FIG. 2A and FIG. 2B, and outputs interpretation results accordingly.

It is noted that that the model shown in FIG. 2B (in which two there are upper and lower lipid layers) typically corresponds to a case in which foreign cells are disposed at the bottom of the lipid layer of the tear film. The lower lipid layer (and the bottom of the upper lipid layer) correspond to the thin cell membrane and the aqueous layer trapped between these two lipid layers corresponds to the water and/or peptides of the inner cell. The algorithm described in FIG. 4 may be applicable to such cases.

The process for detecting physical characteristics of a tear film multilayered tissue, using a hierarchal models-based method, may include the following steps:

running interpretation to fit stack I model of a normal film spectral behavior (e.g. such as shown in FIG. 3), assuming a normal tear film condition, using detected output from the optical detectors and spectral analysis of the received detector output (e.g., where the interpretation is done by assuming a stack I configuration of the subject's tear film and running an approximation algorithm to calculate fit level or any other parameter indicative of the level of approximation/fitness) 41 resulting in a first approximation reflectance value $R_1$ indicative of the level of Reflectance of the measured spectral properties compared to the model of a normal tissue of stack I (herein "stack I model") the interpretation may be a process in which the detectors' output is analyzed to generate information of power/intensity of light reflected from the tear film vs. the wavelength/frequency of the reflected light (herein also "spectral behavior" or "spectral properties" of the reflected light);

assessing/determining thickness of the lipid layer, based on analysis of the received detector output, and checking whether the assessed lipid layer thickness reflectance exceeds a predefined threshold 42 (e.g., a threshold representing a normal tear film reflectance values (e.g. 50 nm) or normal thickness reflectance values that can be achieved within simulation of optional range of typical values such as (e.g., between 20-60 nm)).

if the approximation reflectance value $R_1$ does not defer from a predefined theoretical predicted threshold $R_{th}$ as in step 44, the tear film under test may be automatically considered "normal" i.e. approximated to a stack I configuration and a display may be initiated to the user(s) (e.g. via one or more display output devices of the system such as a screen), for indicating that the tissue under test is normal 43;

if the approximation parameter value does not exceed the predefined threshold 44, further checks may be initiated such as checking whether the slope of the spectral properties of the reflected light in a region between wavelengths of 500-600 nm does not defer from an expected slope threshold S1 45;

if the slope threshold $S_1$ is exceeded in the respective wavelength range of 500-600 nm, the tear film under test may be automatically considered "normal" i.e. approximated to a stack I configuration and a display may be initiated to the user(s) (e.g. via one or more display output devices of the system), for indicating that the tissue under test is normal 43;

if the slope threshold $S_1$ does not exceeded in the respective wavelength range of 500-600 nm, further analysis may be done e.g., by running interpretation to fit stack II 46 e.g., by assuming a stack II configuration (abnormal condition of the tear film) and comparing the measured/deduced spectral properties of the tear film under test to stack II related curve(s) (stack II models) to determine value of each of a plurality of additional approximation parameters values such as stack II model "i" (where multiple models of a stack II state can be available each representing spectral behavior of different combinations of thicknesses of the upper and lower lipid layers and of the intermediate aqueous layer);

In the case that reflectance parameter values do not defer from $R_1$, the tear film under test may be automatically considered "normal" i.e. approximated to a stack I configuration and a display may be initiated to the user(s) (e.g. via one or more display output devices of the system), for indicating that the tissue under test is normal 43;

if the reflectance values $R_{2i}$ is better (e.g. higher) than the first approximation parameter value $R_1$, the best fitted stack II model is selected/determined as the best fit 48; and displaying (outputting) information indicative of the interpretation results 49 such as assessed thickness of each sub-layer of the lipid layer, foreign bodies identification information and characteristics etc., based on the determined best fit model of stack II.

For some applications, techniques described herein are applied to foreign bodies detection (e.g., cells and/or or viruses types that penetrate the lipid layer). In some such cases, a peptide cell is assimilated in the lipid layer, for example, such that a continuous cell layer is formed within the lipid layer. In some such cases, a structure that is generally as shown in FIG. 2B is formed and may be analyzed accordingly. In some cases, foreign bodies accumulate at the bottom of the mucus layer and impact the roughness properties of epithelium layer 390. Typically, such foreign bodies cause changes to the scattering properties of the epithelium layer. Therefore, such cells are detected by detecting the changes in the reflectance that arise from the changes scattering properties.

The approach to situations in which the upper lipid layer has a sub stack that contains foreign cells or bodies on a nanometer level is divided into few different cases and solution to each one is described hereinbelow, as follows.

Measurement of Non-Continuous Layers:

Case 1: Small Bodies with Low Concentration:

In many cases the measured biological tissue will have a non-uniform layer. In these cases, one or more of the stack layers of the biological tissue, for example the tear layers, will be built from partial grouping of structures. A typical example for the tear film is the appearance of very small droplets in the layers. Such droplets can be arranged in a few ways: periodic, random or semi periodic (i.e., periodic with permutations). In some cases the diameter of such droplets may be in the scale of few to tens of nanometers and in other cases they can range up to hundreds of nanometers (e.g., up to 200 nanometers). As long as such structures are small compared to the wavelength of light that used to analyze them, the material can be modeled according to EMA (effective medium approximation) of the physical parameters of the materials that are involved, as is described in the literature, for example in G. A. Nilsson et al., (1981). In this case the optical properties of two materials are evaluated according to the formula:

$$\text{EMA Epsilon} = \text{volume weight ratio 1} * \text{Epsilon}(1) + \text{volume weight ratio 2} * \text{Epsilon (2)} \quad \{\text{Formula 1}\}$$

where:
1 and 2 denote the relevant materials involved in such mix, and epsilon is the dielectric constant of the material $$\text{Epsilon} = N^2 \quad \{\text{Formula 2}\}$$

$$N = n + i*k \quad \{\text{Formula 3}\}$$

n is the refractive index
k is the extinction coefficient of the material.

Formula 1 can be used for calculating the reflectance to good approximation. This approximation hold better mainly in the cases where the structures' sizes are small compared to the wavelengths, the volume weight ratios are small, and the epsilon(1)-epsilon(2)<<EMA Epsilon.

Figure 5A:
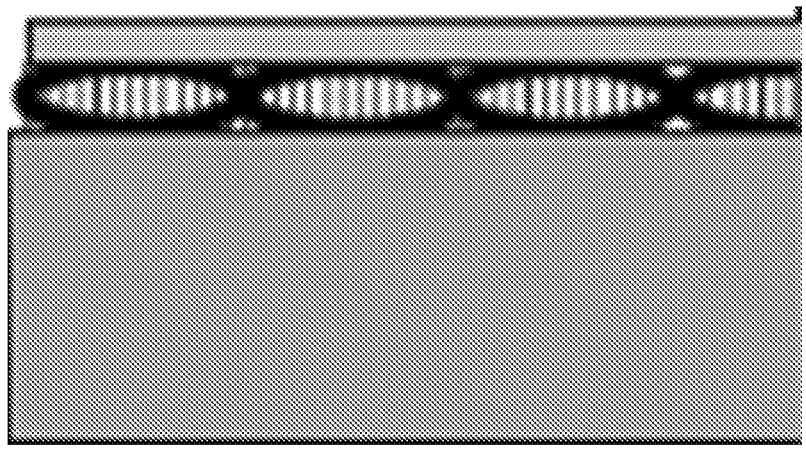
FIGS. 5A, 5B, and 5C are schematic illustrations of respective arrangements of virus cells and/or other small cells within the lipid layer, such cells being detected, in accordance with some applications of the present invention.
Figure 5B:
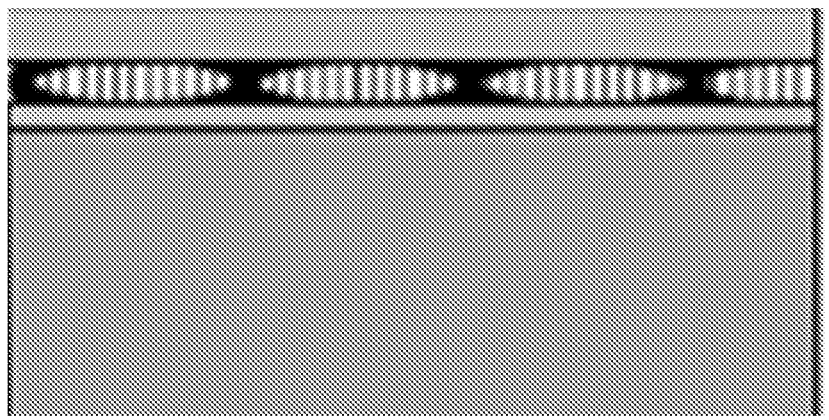
Figure 5C:
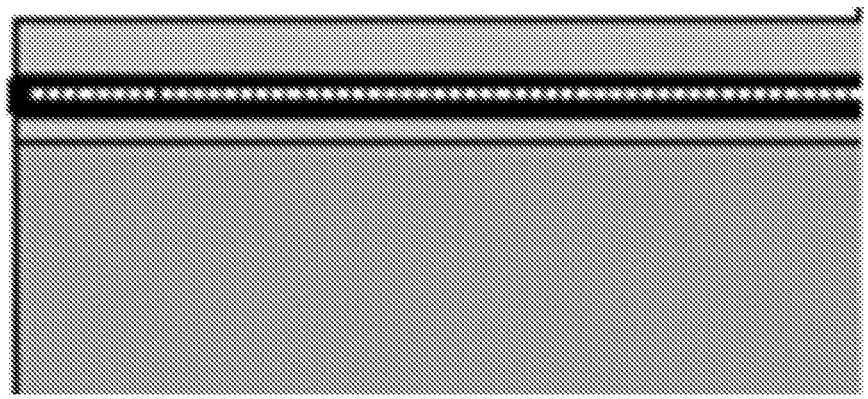

Reference is made to FIG. 5A, which shows foreign bodies (such as cells) captured near the lipid aqueous interface of the tear film of a subject. Reference is also made to FIG. 5B, which is a schematic illustration of an intermediate case in which the foreign bodies are starting to form a near-continuous layer. Reference is further made to FIG. 5C, which is a schematic illustration of a case in which foreign cells form a semi-continuous stack. For some applications of the present invention, the EMA of the mixture of fluids in the tear film is used in order to sense the presence of foreign structures such as droplets or small cells in the tear film, by calculating the spectral reflectance of the tear film. For example, this may be used in cases such as that shown in any one of the FIG. 5A, 5B, or 5C, with this analysis typically being suited to cases in which structures are small compared to the wavelength of light that used to analyze them, as described hereinabove. The refractive index mixture level (the ratio of volume 1/volume 2) may be used as a parameter for the fit algorithm for the detection of the penetration of medium 1 (i.e., the foreign material) into medium 2 (i.e., the native tear film). For some applications, such a case is identified using the algorithm shown in FIG. 6.

Figure 6:
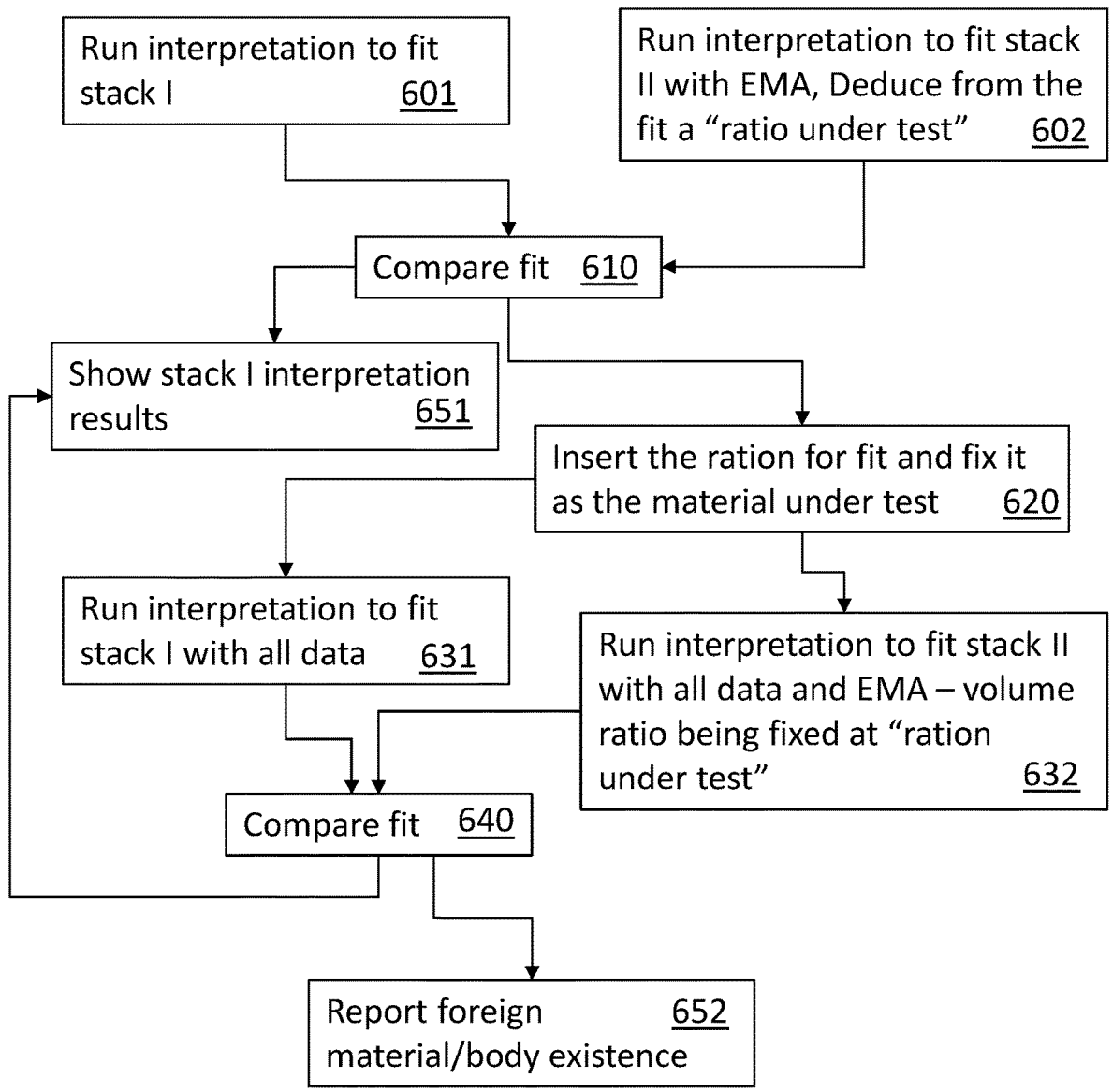
FIG. 6 is a flowchart showing steps of an algorithm that is performed upon a tear film in which small structures are analyzed using EMA (effective medium approximation), in accordance with some applications of the present invention.

Reference is now made to FIG. 6, which is a flowchart showing steps of an algorithm that is performed upon a tear film in which small structures are analyzed using EMA (effective medium approximation), in accordance with some applications of the present invention. Typically, the algorithm is performed by processing module 1200 (FIG. 1). The spectral reflectance of the tear film using the common model is simulated and is fit to the measured one (step 601). A second fit algorithm is performed in parallel (step 602), but this time with an additional parameter which is the volume weight ratio of a suspected foreign body that has penetrated one of the layers of the native tear film, and that is analyzed using Formula 1 provided hereinabove. Subsequently, the fits are compared in step 610. In the case that the second simulated spectral reflectance fit to the measured one is better than the first simulated spectral reflectance, the volume weight ratio is named as "ratio under test" (step 620). Using this "ratio under test", other fits are calculated on a large ensemble of spectral information taken from the same tissue/tear film under test. The level of the fitting using the "ratio under test" is compared to the fitting level of the common model to all measured spectral reflectance (steps 631, 632, 640). If the fitting level is better for all measured spectral reflectance, this comparison determines that the "ratio under test" model is a better selection. Depending on the results the processing module may generate an output indicating that there is a presence of foreign bodies and, optionally, the level of penetration of the foreign bodies (step 652), or the processing module may generate an output indicating zero presence (step 651). This algorithm may also be repeated until a maximum of fitting level is reached, such as to enable determination of the volume weight ratio of the foreign material. It should be noted that by the processing module repeating the algorithm, the processing module may be able to detect even very small structures and small amounts of foreign material, e.g., nano bubbles or even small viruses on the levels of few tens of nanometers.

For some applications, EMA analysis is perturbed by the presence of borders between cells, for example in cases as shown in FIG. 5A (and in some cases of a structure as shown in FIG. 5B). For some applications of the present invention, in such cases, the level of the perturbation may be determined using any one of the four following ways, and/or a combination thereof:

1. Identifying the abnormal (non-specular) scatter levels e.g., by comparing reflectance of low NA reflectance to large NA or use of different apodization schemes. Such mode can be done by controlling a variable aperture during measurement time. For some applications, the variable aperture is an example of an additional optical element 180, described hereinabove 180 with reference to FIG. 1.

2. Identify the "non ideality" level to match specular theoretical reflectance. This can be monitored by the residual errors and may be performed under a minimal noise level state. The error levels point to the fact that the use of the algorithm described hereinabove with reference to Case 1 will not fit and may have large deviation at the final regression fit state.

3. Identify polarization level and obtaining its reflectance by illumination of non-polarized light and compare its polarization to the expected ratio. A straightforward example is the reflectance from stack of layers in normal mode which should have zero effect on the polarization of the reflected light versus the case of the reflectance from non-symmetric droplets or foreign bodies that are arranged in a specific orientation. Such a case of symmetric break may be identifiable, by rotating a polarizer. The need for accurate calibration is minimized due to the fact that the measurement is relative to the base state of non-polarized reflection.

4. Identify the polarization change in time: This option is especially useful when we the processing module performs a series of measurement versus time and the object under test is non-homogeneous. It may be possible to identify any polarization break due to asymmetry of the foreign structures for the case that they are breaking the symmetry and cause polarization changes. Such polarization changes are both relative and self-calibrated.

Case 2: Measurement of Larger Dimensions of Foreign Bodies:

Typically, in the case of larger droplets these structures are much larger than the light wavelength and therefore each structure can be fitted using its own sublayer (stack) model. Typically, the stack will have similar sum of the vertical dimensions. In such cases, there may be relatively small differences between the spectral reflectance of a semi-uniform layer (as shown in FIG. 5C) and the case shown in FIG. 5B.

Case 3. Measurement of Periodic Foreign Materials
Case 3A:

In some cases, the structure that penetrates the layer includes or forms a periodic array. In such a case a known simulation of electromagnetic waves can be used. These calculations from periodic structures are well known in the literature and proved via several calculation options such as RCWA (rigorous coupled wave analysis), Green function, or FDTD (finite difference time domain). Once such simulation is done, it can take into account many of the geometrical dimensions of the layer stack including the periodical patterned array and geometrical parameters. Recurrent use of the simulation can perform a regression and global fit until convergence and best fit is achieved. In this case both the dimensions of the structure, its material and the other layers can be fitted.

Such perfect periodic structures may exist in biologic tissues, however in most of cases they are slightly disturbed. In such cases, the periodicity exists but some deviations from its perfect state are common. Imperfect periodic structure may add small distortions to the measured reflectance compared to the simulated values. However, for small deviations the effect will be negligible. In such cases, the fit will be reasonable and the fit level can be a parameter to describe the deviations. For some applications of the present invention, the existence of periodic or semi-periodic foreign structures in the biological tissue is identified by the fit itself to a simulated electromagnetic wave propagation and by the use of the fitting level (residual errors) of such fit.

Case 3B:

Evaluation of the foreign layer or structure concentration is a meaningful tool in order to evaluate the extent of the phenomena and/or in case of coverage limitations. The concentration level may indicate the level of infection for example or the coverage level of some tissues. In some cases, limited "spot" measurements are more susceptible to varying concentration level which might change during measurement and to encounter this effect an evaluation of the concentration level per measurement might be useful.

Figure 7:
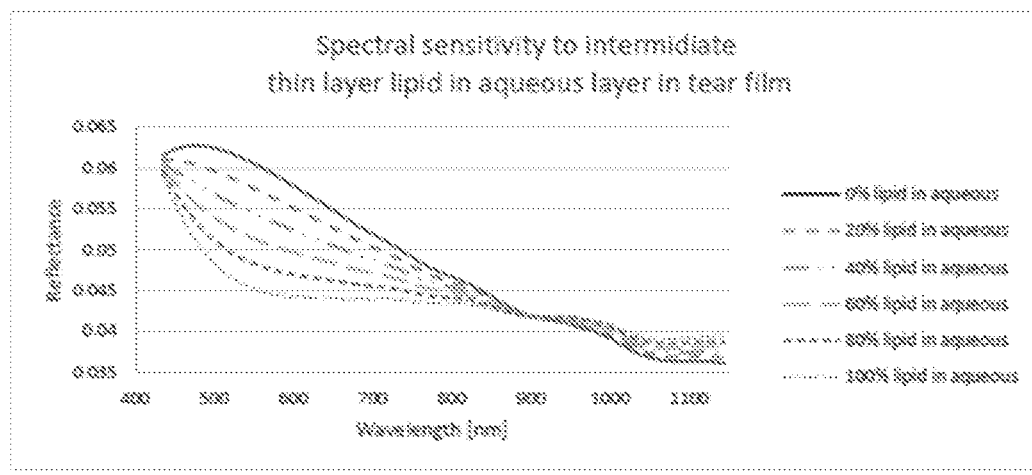
FIG. 7 is a graph showing reflectance versus wavelength for respective ratios of lipid within the aqueous layer, in accordance with some applications of the present invention.

Reference is now made to FIG. 7, which is a graph showing reflectance intensity versus wavelength for respective cases of foreign material or foreign structure area coverage. The curves correspond to cases in which there is non-coherent mix of two signals that come from partial area coverage for the "spot size" area, with one of the signals corresponding to the model shown in FIG. 2A and the other signal corresponding to the model shown in FIG. 2B, with respective curves corresponding to respective levels of area coverage by the model shown in 2B, from 0% to 100% in steps of 20%.

For some applications, the area coverage ratios of the different partial areas' reflectances are simulated and fitted, both in coherent and non-coherent summation of the light amplitudes or intensities from different areas of the measured sampled spot/pixel in the sensors. For some applications, the fit of ratios is fitted in parallel to the thickness values and other parameters that are being measured.

For the non-coherent case, the processing module typically uses Formula 4:

$$I = \text{alpha} \cdot I1 + (1-\text{alpha}) \cdot I2 \quad \{\text{Formula 4}\}$$

where alpha is the area coverage ratio of the area 1 and area 2, and I is the intensity.

For the coherent case, the processing module typically uses Formula 5:

$$r = \text{alpha} \cdot r1 + (1-\text{alpha}) r2 \text{ and } I = |r|^2 \quad \{\text{Formula 5}\}$$

where r is the complex phase dependent reflectance.

A typical case for such summation of the light intensities from different areas of the measured sampled spot in the sensor can be found for the application of Adenovirus penetration to the eye. Epidemic keratoconjunctivitis caused by Human Adenovirus typically begins with viral entry and replication in ocular surface epithelial cells. Since the Adenovirus interacts with the mucus-epithelium interface, for some applications a mix of two models is used; one with normal eye roughness and the other with roughness that is being disturbed by the virus. In this manner, penetration of the mucus-epithelium interface and changes in this penetration over time may be detected even from early stages of the infection.

Case 3C:

In the cases where a variable aperture is being used (e.g. as additional optical element 180, shown in FIG. 1), the use of low NA versus high NA illumination and/or light detection can be used for evaluating the level of light that was scattered. Such light can be scattered when the structures within the tissue are not planar and create abrupt interface. In these cases, the light will not reflect in specular mode and light will be lost especially when using low NA. The low NA configuration typically uses a small aperture to illuminate the tissue and/or collects the scattered light from the tissue in a very narrow angles. The light lost from non-specular reflection is large in low NA in comparison to using high NA. Changes in the ratios between these two modes can supply information on the existence of scattering due to the foreign objects. Note the variable aperture can be placed in the illumination path, imaging path or both. Note that such scatter can be noticed both for a periodic or a random situation.

For some applications, low NA reflectance measurements are used, in order to evaluate the existence of small topography changes caused by one of the layers of the stack. Such topography typically causes slopes that deflect specular rays that are generated at edges of borders. Such slopes typically deflect light from being captured by the low NA optics and therefore cause a local light reflection reduction. A typical case is the Adenovirus penetration through the mucus epithelium after few days. This may result in blisters of the epithelium that impact its topography, which comes from viral entry and replication in ocular surface epithelial cells, followed by infected stromal corneal cells.

For some applications, a low NA is used in the illumination path such that a narrow illumination beam is generated. By directing a narrow illumination beam toward the tissue, the sensitivity of the small changes in the surface topography may be enhanced, such that even submicron penetration of foreign bodies is detectable.

Case 3D:

When a polarizer is used and is rotated between two or more states of polarizations, the polarization ratio can be measured and be used as an indicator for the presence of foreign cells or small bodies that are involved in the polarization effect. Hence, for the case where there is a symmetry break to the structure of these bodies (e.g., due to asymmetrical foreign bodies), fast rotation of the polarization state of light may be performed. Measurements from respective polarization states are subtracted from one another in order to provide information on the asymmetrical structures in the layer. The polarizers can be inserted in the illumination path, the imaging path or in both. In some applications, a first polarizer is placed the illumination path and a second polarizer is placed in the imaging path, and measurements are performed in cross-polarization mode (i.e., such that there is one known polarized light illuminating the tissue while the collection is performed at a different state of polarization). In such cases, the measurement of light is indicative of the polarization change by the tissue. Such polarization changes by the tissue is indicative of the presence of non-symmetrical structures.

Case 4: Dynamic Trends Evaluation for Diagnosis of Foreign Bodies or Materials

Figure 8:
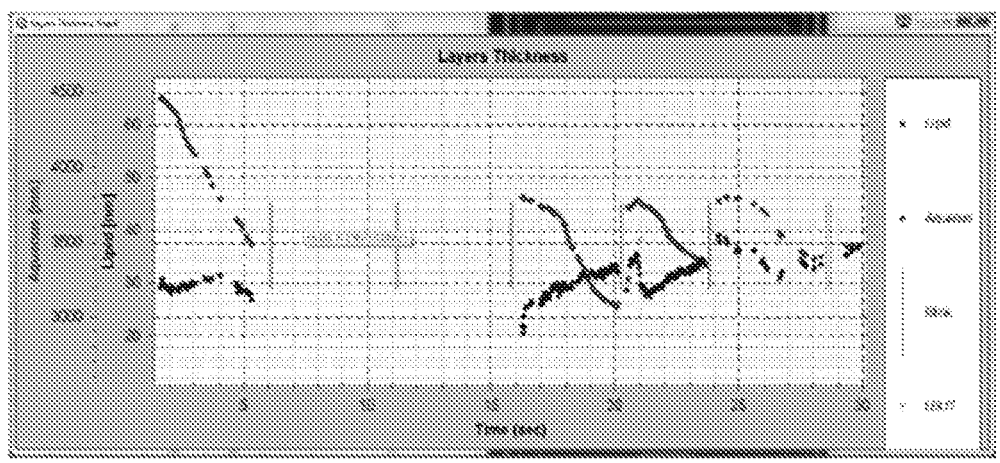
FIG. 8 is a tear-film imager trend chart showing changes of lipid-layer thickness and aqueous-layer thickness over time, as measured in accordance with some applications of the present invention.

Reference is now made to FIG. 8, which is a tear-film imager trend chart showing changes of lipid-layer thickness and aqueous-layer thickness over time, as measured, in accordance with some applications of the present invention. The thickness measurements are typically the outcome of the steps described hereinabove. In FIG. 8, the lipid layer thickness values are marked in a first shade and they present relatively stable behavior across the blink to blink time, varying as a relatively flat curve or in a monotonic slow increase over most of the measurement time. In the case shown in FIG. 8, the lipid layer average thickness is 32 nanometers +−4 nm. However, after 21 seconds there is an abrupt fall of the thickness value of the lipid layer. This fall can be recognized in comparison to the short-term previous thickness values. Once the flat or monotonic change has a sharp downfall change a break event is declared. This event is named as lipid break up time (LBUT) and it is associated with the time period from previous blink end to the break event time. Such an event (which was found via the measurement steps described hereinabove) indicates that some change in the layer or one of the underlayers has happened. For some applications of the present invention, such an abrupt change in the thickness of the lipid layer is interpreted by the processing module as being indicative of there having been a change in the structure of the tear-film layers. In accordance with some application, such an indication may be determined not only via the layer thickness values, but also via the reflectance values or the fit levels between model and measurement, or any other trend change, including changes such as a change in the image color ratios or contrast variations per group of ROI (region of interest) pixels. For the case of partial coverage of the area by structures or cells, it is natural to see reflectance values changing over time, due to the optional partial coverage of the spot size area (e.g., as described hereinabove with reference to FIG. 7).

Figure 9:
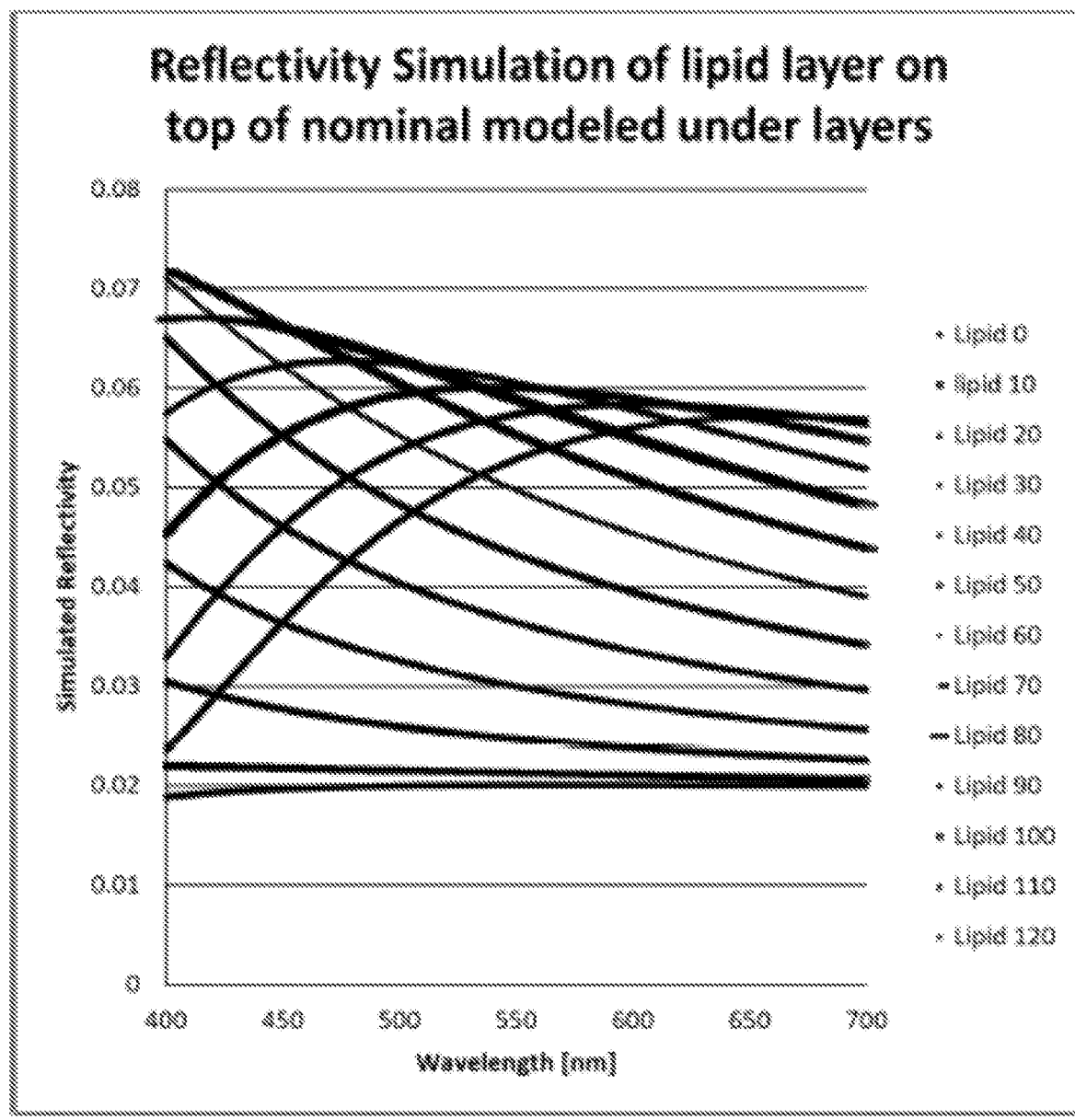
FIG. 9 is a graph showing results of a simulation that demonstrates the color intensity ratio (or spectral dependence) of reflected light from the upper lipid layer on the thickness of the upper lipid layer, as measured in accordance with some applications of the present invention.

Case 5: Thickness Mapping for Diagnosis of Foreign Bodies or Materials:

Reference is now made to FIG. 9, which is a graph showing results of a simulation that demonstrates the color intensity ratio (or spectral dependence) of reflected light from the upper lipid layer on the thickness of the upper lipid layer.

Figure 10A:
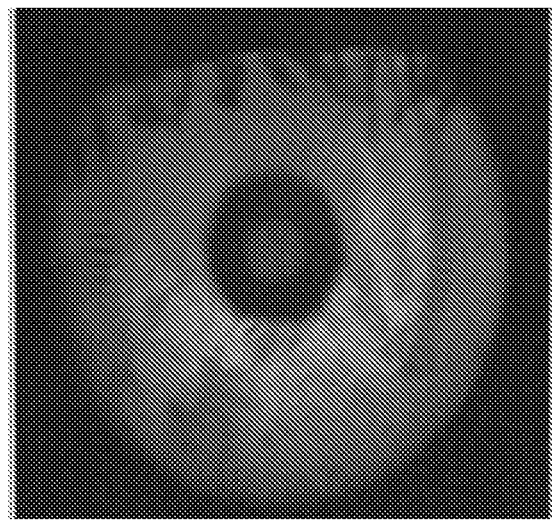
FIGS. 10A and 10B show images of an eye of a subject where.
Figure 10B:
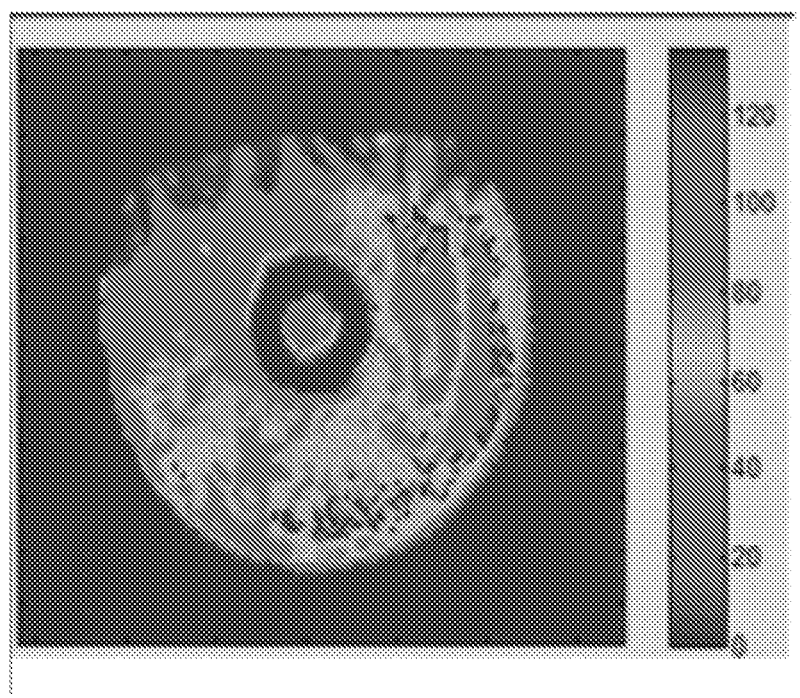

Reference is also made to FIGS. 10A and 10B showing images of an eye of a subject where: FIG. 10A shows a raw image of an eye with two grids indicated over the raw eye image, and FIG. 10B shows an image display of a lipid layer thickness color map disposed over the eye image such as to show thicknesses of the lipid layers over their corresponding locations in the cornea surface, where each color represents a different thickness value or thickness values range.

As indicated in FIGS. 10A and 10B, for a healthy eye, the color intensity ratios of the reflected light are attributed to lipid thickness values. The values are determined using the calculated theoretical camera intensities obtained from the reflectance model of the measured lipid layer multiplied by the known transmission function of the optical system per each camera pixel. The theoretical values may be calculated using the appropriate model of the lipid layer and are fit to the actual measured subpixels intensity. The outcome is the thickness of the lipid at a certain point by a best fit match. In the case that the model of the healthy eye is wrong or in the case that there is another model that should be applied the fitting errors typically increase. Therefore, for some application, the processing module determines that a different model of the eye should be used that takes into account additional variables such as the presence of a foreign body (which may be identified using the techniques described hereinabove, e.g., with reference to the algorithms shown in FIGS. 4 and 6). Such a model may account for a foreign layer, cell, or group of structures. For some such applications, the processing module generates a map of the eye that includes an indication of the foreign body, and/or that accounts for the foreign body in the lipid layer thickness map.

For some such applications, the processing module identifies the pixels that have large errors in relation to the current model, or the pixels that should use a different model and attributes the erroneous pixels to diagnosis of foreign layer, cells, or structures in the relevant tissue.

Typically, there is an assumption that lateral changes in the thickness values are moderate. Therefore, for some applications, in response to detecting an abrupt lateral change in the lipid layer thickness values (and/or in the error of fit), the processing module attributes this to the presence of a foreign body at that location.

For some applications, polarization maps of the tear film are acquired using fast polarization rotation, e.g., using methods as described hereinabove. The difference between the polarization maps are mapped and attributed to symmetry violation due to non-symmetrical structures in the tissue's layers.

According to some embodiments, as a result of the performing the steps described hereinabove, the processing module may be configured to determine quantitative parameters such as the foreign body thickness, dimensions, periphery walls, width, length, envelope thickness, polarization artifacts (e.g., the amount of polarization rotation), and/or or other attributes. For some applications, the processing module outputs such quantitative parameters, such that a user is able to determine the type of foreign body that is present. Alternatively or additionally, the processing module may automatically determine which type of foreign bodies are present, based upon the above-mentioned parameters. For example, it is well known that viruses are much smaller than most cells and can be as small as 100 nanometers diameter. Accordingly, when measuring a foreign body with a diameter or thickness in similar range, such as 50 to 150 nanometers, the processing module may generate an output indicating that there is a relatively high probability of a presence of a virus in the tear film, and/or may generate an indication of the type of virus.

Applications of the invention described herein can take the form of a computer program product accessible from a computer-usable or computer-readable medium (e.g., a non-transitory computer-readable medium) providing program code for use by or in connection with a computer or any instruction execution system, such as a processing module 1200 (FIG. 1), which may be in communication with the optical subsystem. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Figure 11:
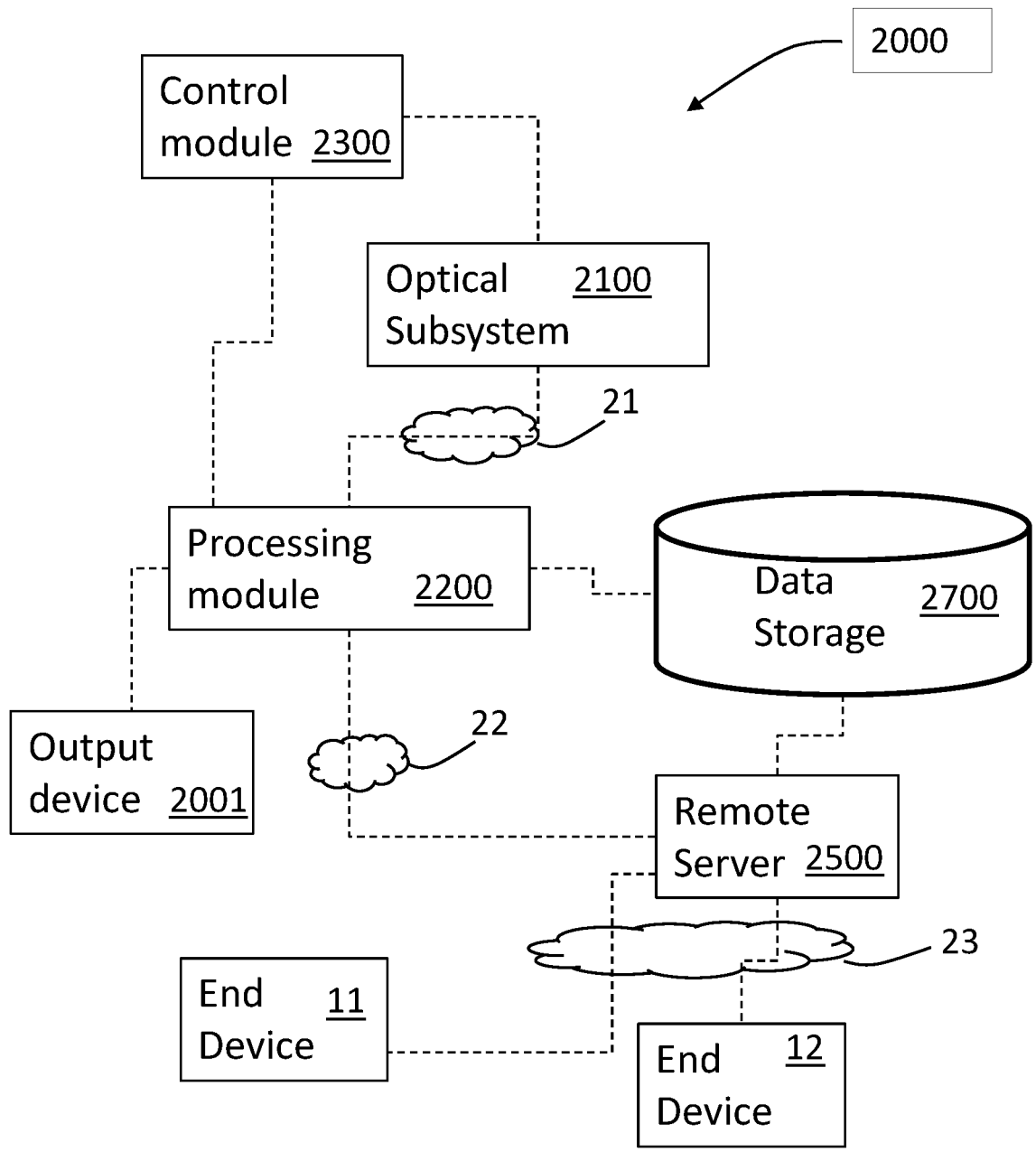
FIG. 11 shows a block diagram, schematically illustrating modules of a system for detecting physical characteristics of a multilayered tissue, using known spectral models, according to some embodiments of the invention.

Reference is now made to FIG. 11, showing a block diagram, schematically illustrating modules of a system 2000 for detecting physical characteristics of a multilayered tissue, using known spectral models, according to some embodiments of the invention. The system 2000 may be used for handling and supporting multiple subjects and/or multiple types of multilayered tissue detection and diagnosis.

According to these embodiments, as illustrated in FIG. 11, the system 2000 may include at least:

- an optical subsystem 2100 including for example one or more light sources such as a light source configured for irradiating light in the VIS and optionally also in the NIR wavelengths bands, one or more optical detectors such as a spectrometer, a camera, an interferometer and the like and means for directing light from the light source(s) and/or the tissue towards the optical detector(s);
- a processing module 2200 operatively associated with the optical subsystem 2100, the processing module 2200 being configured at least to:
  - (i) receive detector-output of each optical detector, indicative of optical properties of light reflected or deflected from the respective multilayered tissue;
  - (ii) analyze the received detector-output to determine spectral properties of the multilayered tissue; and
  - (ii) determine a best-fit model from plurality of spectral models of the respective multilayered tissue, each model representing different physical characteristics of the respective multilayered tissue, the determination of the best-fit model being done based on determination of best-fit of spectral properties of the model to the determined spectral properties of the multilayered tissue;
  - (iv) determine physical characteristics of the multilayered tissue, based on the determined best-fit model; and
  - (v) output information indicative of the determined physical characteristics of the multilayered tissue such as thickness of layers thereof, detected foreign bodies information etc., via one or more output devices;
- a control module 2300, operatively associated with the optical subsystem 2100 and the processing module 2200, for enabling control over devices of the optical subsystem 2100 such as light sources control, autofocusing control, imaging selection control, detectors control etc., and for enabling control on other devices such as output devices etc., the control module 2300 and/or the processing module 2200 may support a user interface for allowing information/data input and display for controlling the optical subsystem, the analysis process and/or presentation of the information;
- a data storage 2700 for storage of subjects' information such as, for example, subjects personal and medical details (name, gender ID number, weight, height etc. and medical history related details), models groups, wherein each models group may be associated with a different type of multilayered tissue and/or a different area/layer of the multilayered tissue; and
- one or more output devices (e.g. one or more visual display devices such as a screen 2001 and/or auditory display devices such as a speaker).

According to some embodiments, the optical subsystem 210, the processing module 2200, and the control module 2300 may be configured for transmitting data therebetween such as control commands to the optical subsystem 2100, to some embodiments, the system 2000 may further be associated with or include one or more remote servers such as remote server 2500 (e.g. cloud server), wherein the processing module 2200 may include one or more software and/or hardware means for processing the detector-output and determining physical characteristics of tissues, and may be operable via the remote server 2500. Alternatively, the processing module 2200 may be embedded or operated by a computer device that is located in the vicinity of the optical subsystem 2100 and communicate therewith via a first communication network 21 while communicating also with the remote server 2500 via a second communication network 22.

In some embodiments, the remote server 2500 and/or the processing module 2200 may enable communication with one or more remote end devices via a third communication networking 23 such as end devices 11 and 12, for enabling display of subjects' information to more than one remotely located users (e.g., via a designated application that can be installed/downloaded/uploaded to the end device.

According to some embodiments, the data storage 2700 may be part of the remote server 2500 or a computer device operating the processing module 2200.

Figure 12:
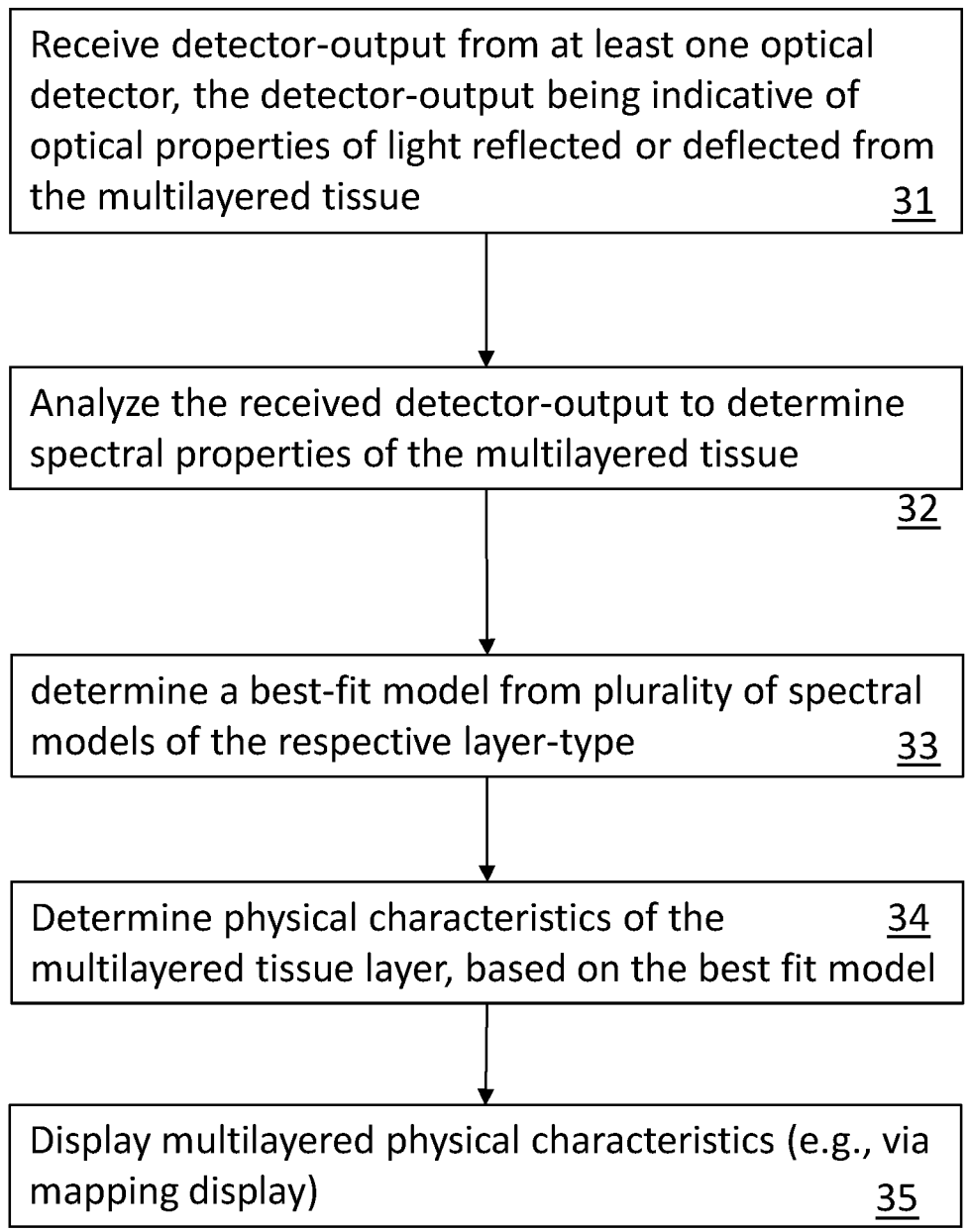
FIG. 12 shows a flowchart, schematically illustrating a process/method for detecting physical characteristics of a multilayered tissue, using known spectral models, according to some embodiments of the invention.

Reference is now made to FIG. 12, schematically illustrating a process/method for detecting physical characteristics of a multilayered tissue, using known spectral models, according to some embodiments of the invention, the process including at least the following steps of:

- receiving detector-output from one or more optical detectors 31, the detector output being indicative of optical properties of light reflected/deflected from a multilayered tissue being tested;
- analyzing the received detector-output to determine spectral properties of the multilayered tissue 32;
- determining a best fit model from a plurality (at least two) of known models of the same tissue type 33;
- determining physical characteristics of the multilayered tissue, based on the determined best fit model 34; and
- display information (e.g. visually) indicative of the determined physical characteristics of the multilayered tissue 35.

Figure 13:
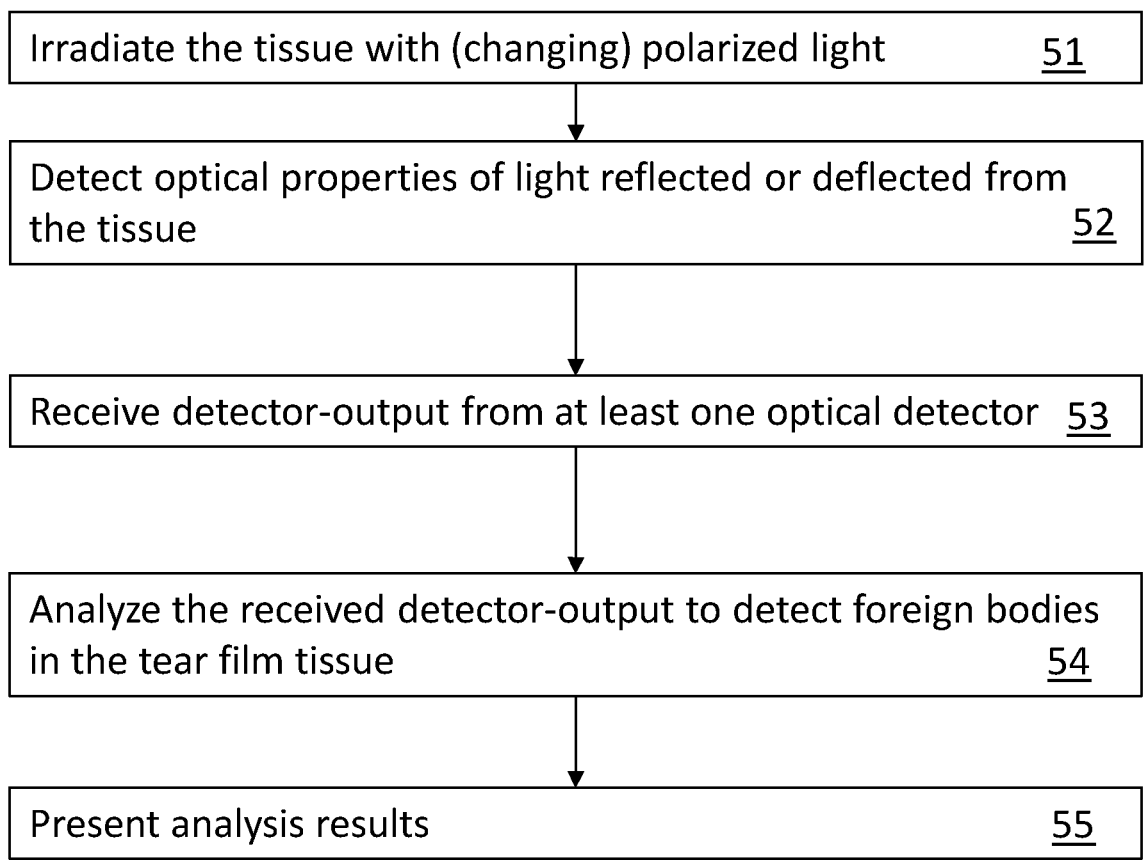
FIG. 13 shows a flowchart, schematically illustrating a process/method for detecting physical characteristics of a multilayered tissue, by identification of optical characteristics of light reflected from the tissue, the optical characteristics including at least polarization changes of reflected/deflected light from the tissue, according to some embodiments of the invention.

Reference is now made to FIG. 13, schematically illustrating a process/method for detecting physical characteristics such as foreign bodies or accumulated materials in a multilayered tissue such as a tear film tissue, by identification of optical characteristics of light reflected from the tissue, the optical characteristics optionally including polarization changes of reflected/deflected light from the multilayered tissue, according to some embodiments of the invention. This method may include at least part of the following steps:

- irradiating the multilayered tissue with light in the VIS and NIR bands while changing polarization of the irradiated light (e.g. by using a movable polarizer) 51;
- detecting optical properties of light reflected/deflected from the cornea of the subject, using t least one optical detector 52;
- receiving the detector-output from each of the optical detectors being used, the detector-output being indicative of the detected optical properties of the tear film 53;
- analyzing the received detector-output to detect foreign bodies and/or accumulated materials such as droplets of one or more different materials/substances in the tear film (e.g., specifically in the lipid layer of the tear film, using one or more analysis techniques such as the EMA technique as described hereinabove) 54; and
- presenting analysis results 55 via one or more output devices.

Aspects of disclosed embodiments pertain to systems and methods for determining physical characteristics of a multilayered tissue such as a tear film by measuring optical (e.g., spectral) properties of light reflected/deflected from the tissue (e.g. tear film), and using one or more remotely located communication and/or computation devices such as one or more remotely located end devices and/or servers (in respect to location of the optical subsystem detecting the optical properties of the tissue), configured to analyze the detector-output and to display analysis results via display means (such as screens) of the end devices, using a main server unit comprising one or more servers for online/cloud based communication, data storage and data processing.

EXAMPLES

Example 1 is a system for detecting physical characteristics of a multilayered tissue of a subject, the system comprising:
an optical subsystem comprising at least:
a broadband light source configured and positioned to directly or indirectly illuminate the multilayered tissue; and
at least one optical detector, configured and positioned to optically detect one or more optical properties of the multilayered tissue; and
a processing module operatively associated with the optical subsystem, the processing module being configured to: (i) receive detector-output from the at least one optical detector; (ii) determine spectral properties of the multilayered tissue by processing the received detector-output; and (iii) determine physical characteristics of the multilayered tissue by using multiple spectral models of the of the multilayered tissue comprising at least: a first model assuming a normal condition of the multilayered tissue and one or more additional models, assuming abnormal conditions of the multilayered tissue, each model being associated with different spectral properties, wherein physical characteristics of the multilayered tissue are determined by hierarchal determination of a best-fit model from the multiple spectral models, based on determination of best-fit of spectral properties of the respective model to the determined spectral properties of the multilayered tissue.

In example 2, the subject matter of example, may include, wherein the processing module is configured to determine the physical characteristics of the multilayered tissue by comparing spectral properties of the reflected light to spectral properties of the first model and of the one or more additional models within at least one predefined wavelengths range in which spectral properties of the reflected light is distinctively different for different conditions of the multilayered tissue.

In example 3, the subject matter of any one or more of example 2 may include, wherein the spectral properties comprise the behavior of the intensity of the reflected light in respect to the wavelength of the reflected light.

In example 4, the subject matter of any one or more of examples 2 to 3 may include, wherein the wavelengths range is between 450 nm to 650 nm or between 500 nm to 600 nm.

In example 5, the subject matter of any one or more of examples 1 to 4 may include, wherein the physical characteristics of the multilayered tissue comprise one or more of:
thickness of at least one layer of the multilayered tissue;
thickness of at least one area of at least one layer of the multilayered tissue;
foreign bodies types, dimensions, coverage, material, concentration, roughness, periodical level, and/or thickness;
accumulated structures' configuration, dimensions and/or periodicity level;
layers arrangement;
differences in thicknesses of areas of a layer or a sub layer of the multilayered tissue.

In example 6, the subject matter of any one or more of examples 1 to 5 may include, wherein the at least one optical detector comprises at least one of: a spectrometer, an interferometer, a color camera, a color sensor, wherein the processing module is configured to combine output of all optical detectors being used for improving determination of spectral properties of the multilayered tissue, areas and/or layers thereof.

In example 7, the subject matter of any one or more of examples 1 to 6 may include, wherein the at least one optical detector is configured at least for detecting light in the near infrared (NIR) and/or visible (VIS) wavelength bands.

In example 8, the subject matter of any one or more of examples 1 to 7 may include, wherein the system is further configured for detection of physical characteristics of a tear film multilayered tissue, wherein the layer-types of the tear film comprise at least: a lipid layer, aqueous layer, mucus layer and a rough epithelium layer, wherein the first model of the tear film is associated with spectral properties of a normal tear film condition in which the lipid layer is continuous and within a predefined thickness range and the one or more additional models represent spectral properties of a tear film of abnormal conditions in which the lipid layer is disrupted by at least one intermediate layer or foreign bodies.

In example 9, the subject matter of example 8 may include, wherein models representing spectral characteristics of the lipid layer are indicative of one or more of:
different thicknesses of the lipid layer;
different thicknesses of the one or more inner sublayers in the lipid layer;
thicknesses of upper and lower lipid layers and thickness of the at least one intermediate layer, in cases in which the lipid layer is separated by an intermediate layer;
dimensions, size, arrangement and/or material types of one or more foreign bodies and/or of one or more accumulated droplets.

In example 10, the subject matter of any one or more of examples 8 and 9 may include, wherein each of the spectral models represents behavior of intensity of reflected light (light reflected from the tear film i.e. from the subject's cornea) in respect to wavelength of the reflected light.

In example 11, the subject matter of any one or more of examples 8 to 10 may include, wherein the optical subsystem is further configured to direct at least a portion of light emanating from the light source towards the cornea of the eye of the respective subject for measuring optical characteristics of the subject's tear film tissue and to direct at least a portion of light reflected and/or deflected from the subject's cornea towards each of the at least one optical detector.

In example 12, the subject matter of example 11 may include, wherein the optical subsystem is further configured to assist in achieving optimal relative optical position of a point or area of the surface of the cornea of the subject in respect to at least one optical axis of the optical subsystem by using imaging means of the optical subsystem, to form at least one image over the subject's cornea surface; and/or directing subject's gaze.

In example 13, the subject matter of example 12 may include, wherein the optical subsystem comprises one or more grid elements for forming a grid image over the subject's cornea surface, for achieving desired relative position between the subject's cornea and the at least one optical axis of the optical subsystem.

In example 14, the subject matter of any one or more of examples 12 to 13 may include, wherein the optical subsystem further comprises a reticle and/or a head support, for assisting a subject in directing his/her gaze for preventing or reducing the subject from moving his/her head and/or from shifting his/her gaze from a single gazing axis.

In example 15, the subject matter of any one or more of examples 1 to 14 may include, wherein the system further comprises at least one remote computation and communication device configured for:
  communication with the processing module for any one or more of: retrieval of models, receiving of detector-output from the at least one optical detector, for remote output data processing and analysis, transmission of messages to one or more additional end devices via one or more communication networks;
  data processing of received data for determining or identifying physical characteristics of the respective multilayered tissue;
  transmission of messages to remote end devices of users;
  presentation of information indicative of determined physical characteristics of the multilayered tissue of each subject and for each tissue via one or more output devices, and/or for presentation of subjects' personal and medical information;
  data storage module for storage of subjects' related information.

In example 16, the subject matter of any one or more of examples 1 to 15 may include, wherein the system further comprises one or more output devices for presentation of the information indicative at least of determined physical characteristics of the respective multilayered tissue.

In example 17, the subject matter of example 16 may include, wherein information presented comprise an image of the tissue and an image of a color-map representing the physical characteristics of the tissue as detected.

In example 18, the subject matter of any one or more of examples 1 to 17 may include, wherein the processing module is remotely or locally located in respect to the optical subsystem and configured for remote, short-distance, wireless and/or wired communication with each of the optical detectors and with the light source.

In example 19, the subject matter of any one or more of examples 1 to 18 may include, wherein the processing module is further configured to use any one or more of the following iterative techniques to determine a tear film tissue physical characteristic: Simplex, Steepest Decent, Stimulated annealing, Levenberg-Marquardt algorithm.

In example 20, the subject matter of any one or more of examples 1 to 19 may include, wherein the processing module is further configured to use an effective medium approximation (EMA) method to identify small bodies in its lipid layer of a tear film multilayered tissue, for identification of small bodies that are smaller in size than the smallest wavelength of the light source.

In example 21, the subject matter of any one or more of examples 1 to 20 may include, wherein the at least one optical detector comprises at least a spectrometer and a camera, and wherein the optical subsystem further comprises a narrow-band filter, disposed between the light source and the camera, for reducing or correcting ambiguity in output image of the spectrometer caused due to the interference cycles.

In example 22, the subject matter of any one or more of examples 1 to 21 may include, wherein the optical subsystem is configured to automatically perform optical measurements, by automatically control optical detectors acquisition and autofocusing and/or wherein the processing module is configured for automatic processing of the received detector-output and presenting of resulting information related to determined physical characteristics of the multilayered tissue.

In example 23, the subject matter of any one or more of examples 1 to 22 may include, wherein the optical subsystem further comprises any one or more of: focusing means, collimating means, diffractive means, polarizing means, one or more beam splitters, filtering means, for causing light, emanating from the light source and/or reflected/deflected from the multilayered tissue to be optically directed and/or manipulated such as to optimize the determination of the optical characteristics of the tissue as detected by the at least one optical detector and/or to optimize detector-output analysis performances.

In example 24, the subject matter of example 23 may include, wherein the optical subsystem further comprises at least one polarizing element positioned in relation to multilayered tissue such as to enable polarization of light emanating from the at least one light source, for detecting physical characteristics of the tissue including at least detection of foreign structures.

In example 25, the subject matter of example 24 may include, wherein the polarizing element is rotatable for enabling detection of foreign structures by detection of asymmetrical changes in polarization of light reflected from the multilayered tissue.

In example 26, the subject matter of any one or more of examples 1 to 25 may include, wherein the processing module is further configured to control display of the determined physical characteristics of the multilayered tissue, via one or more output devices including at least one visual display device and/or at least one audio display device.

In example 27, the subject matter of example 26 may include, wherein the processing module is further configured to transmit information indicative of determined physical characteristics of the multilayered tissue to one or more remotely located servers and/or end devices for displaying the information therethrough.

In example 28, the subject matter of any one or more of examples 26 to 27 may include, wherein the processing module is further configured to support a user interface operable via one or more end devices, enabling users to input information relating to a multilayered tissue of a specific subject, subject's information, and/or display information associated with the determined physical characteristics of the multilayered tissue of the respective subject.

Example 29 is a method for detecting physical characteristics of a multilayered tissue of a subject, the method comprising at least the steps of:
  receiving detector-output from at least one optical detector, the detector-output being indicative of optical properties of light reflected or deflected from the respective multilayered tissue;
  analyzing the received detector-output to determine spectral properties of the multilayered tissue; and
  determining physical characteristics of the multilayered tissue by using multiple spectral models of the of the multilayered tissue comprising at least: a first model assuming a normal condition of the multilayered tissue and one or more additional models, assuming abnormal conditions of the multilayered tissue, each model being associated with different spectral properties, wherein physical characteristics of the multilayered tissue are determined by hierarchal determination of a best-fit model from the multiple spectral models, based on determination of best-fit of spectral properties of the respective model to the determined spectral properties of the multilayered tissue.

In example 30, the subject matter of example 29 may include, wherein the determining of the physical characteristics of the multilayered tissue is done by comparing spectral properties of the reflected light to spectral properties of the first model and of the one or more additional models within at least one predefined wavelengths range in which spectral properties of the reflected light is distinctively different for different conditions of the multilayered tissue.

In example 31, the subject matter of example 30 may include, wherein the spectral properties comprise the behavior of the intensity of the reflected light in respect to the wavelength of the reflected light.

In example 32, the subject matter of any one or more of examples 30 to 31 may include, wherein the wavelengths range is between 450 nm to 650 nm or between 500 nm to 600 nm.

In example 33, the subject matter of any one or more of examples 29 to 32 may include, wherein the physical characteristics of the multilayered tissue comprise one or more of:
  thickness of at least one layer of the multilayered tissue;
  thickness of at least one area of at least one layer of the multilayered tissue;
  foreign bodies dimensions, coverage, material, concentration, roughness, periodical level, and/or thickness;
  accumulated structures' configuration, dimensions and/or periodicity level;
  layers arrangement;
  differences in thicknesses of areas of a layer of the multilayered tissue.

In example 34, the subject matter of any one or more of examples 29 to 33 may include, wherein the at least one optical detector comprises at least one of: a spectrometer, an interferometer, a color camera, a color sensor, wherein the analysis of the detector output is done by to combining output of all optical detectors being used for improving determination of spectral properties of the multilayered tissue, areas and/or layers thereof.

In example 35, the subject matter of any one or more of examples 29 to 34 may include, wherein the multilayered tissue comprises a tear film, wherein the layer-types of the tear film comprise at least: a lipid layer, aqueous layer, mucus layer and a rough epithelium layer, wherein the models of the lipid layer-type are associated with one of two optional lipid layer states: a first lipid layer state in which the lipid layer is continuous and a second lipid layer state having one or more inner sublayers withing the lipid layer.

In example 36, the subject matter of example 35 may include, wherein models representing spectral characteristics of the lipid layer are indicative of one or more of:
  different thicknesses of the lipid layer;
  different thicknesses of the one or more inner sublayers in the lipid layer;
  thicknesses of upper and lower lipid layers and thickness of intermediate aqueous layer, in cases in which the lipid layer is separated by an intermediate aqueous layer;
  dimensions, size, arrangement and/or material types of one or more foreign bodies and/or of one or more accumulated droplets.

In example 37, the subject matter of any one or more of examples 35 and 36 may include, wherein each of the spectral models represents behavior of intensity of light reflected from the cornea of the subject vs. wavelength of the reflected light for each modeled state of the lipid layer associated with the respective model.

In example 38, the subject matter of any one or more of examples 35 to 37 may include, wherein the method further comprises directing at least a portion of light emanating from the light source towards the cornea of the eye of the respective subject for measuring optical characteristics of the subject's tear film tissue and to direct at least a portion of light reflected and/or deflected from the subject's cornea towards each of the at least one optical detector.

In example 39, the subject matter of example 38 may include, wherein the method further comprises:
  assisting in achieving optimal relative optical position of a point or area of the surface of the cornea of the subject in respect to at least one optical axis of the optical subsystem by using imaging means of the optical subsystem, for forming an image over the subject's cornea surface;
  directing subject's gaze; and/or
  supporting the subject's head during detection time.

In example 40, the subject matter of any one or more of examples 29 to 39 may include, wherein the method further comprises at least one of:
  supporting communication between the light source, the at least one detector and the processing module and with one or more remote computation and communication devices, for any one or more of: retrieval of models, receiving of detector-output from the at least one optical detector, for remote output data processing and analysis, transmission of messages to one or more additional end devices via one or more communication networks;
  transmitting of messages indicative of tissue characteristics of one or more subjects to one or more remote end devices of users;
  presenting information indicative of determined physical characteristics of the multilayered tissue of each subject and for each tissue via one or more output devices, and/or for presentation of subjects' personal and medical information;
  data storing for storage of subjects' related information.

In example 41, the subject matter of any one or more of examples 29 to 40 may include, wherein the determination of the one or more spectral characteristics of the multilayered tissue comprises using any one or more of the following iterative techniques: Simplex, Steepest Decent, Stimulated annealing, Levenberg-Marquardt algorithm.

In example 42, the subject matter of any one or more of examples 29 to 41 may include, wherein the method further comprises using an effective medium approximation (EMA) method to determine best fit model for a tear film multilayered tissue having small bodies in its lipid layer that are smaller in size than the wavelengths of the light source.

In example 43, the subject matter of any one or more of examples 29 to 42 may include, wherein all optical measurements, analysis and presenting of analysis results is done automatically and controlled via a control module.

Example 44 is a method for detecting physical characteristics of a multilayered tissue of a subject, the method comprising at least the steps of:
  irradiating a multilayered tissue using at least one light sources;

detecting optical properties of light reflected or deflected from the respective multilayered tissue, using at least one optical detector outputting detector-output, the optical properties of the tissue comprising at least polarization of light reflected or deflected from the multilayered tissue; and determining physical characteristics of the multilayered tissue, based on the optical properties thereof.

In example 45, the subject matter of example 44 may include, wherein the identification of polarization of the reflected or deflected light is done by using at least one polarizer and a mechanism that is configured for changing the polarization over time of light emanating from the light source or reflected/deflected from the multilayered tissue.

In example 46, the subject matter of example 45 may include, wherein the polarizer is rotatable for enabling detection of foreign structures in a tear film multilayered tissue, by detection of asymmetrical changes in polarization of light reflected from the multilayered tissue.

Examples of a computer-readable medium include a semiconductor or solid-state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor (e.g., computer processor) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters. For some applications, the storage and the relevant interpretation can be done in remote using fast communication mode based on direct link or web based links such as physical network line, WiFi, Bluetooth, or cellular. For some applications, at least some of the interpretation steps described hereinabove are performed at a remote server.

Computer program code for carrying out operations of the present invention may be written in any combination of one or more programming languages, including an object oriented programming language such as Java, Smalltalk, C++ or the like and conventional procedural programming languages, such as the C programming language or similar programming languages.

It will be understood that the algorithms described herein, can be implemented by computer program instructions. These computer program instructions may be provided to a processor of a general purpose computer, special purpose computer, or other programmable data processing apparatus to produce a machine, such that the instructions, which execute via the processor of the computer (e.g., processing module 1200) or other programmable data processing apparatus, create means for implementing the functions/acts specified in the algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the flowchart blocks and algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the algorithms described in the present application.

Processing module 1200 may be a hardware device programmed with computer program instructions to produce a special purpose computer. For example, when programmed to perform the algorithms described herein, processing module 290 typically acts as a special purpose tissue-analysis processing module. Typically, the operations described herein that are performed by processing module transform the physical state of a memory, which is a real physical article, to have a different magnetic polarity, electrical charge, or the like depending on the technology of the memory that is used. For some applications, operations that are described as being performed by a processing module are performed by a plurality of processing modules in combination with each other.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

Steps of methods and/or processes disclosed herein may be at least partially implemented as a computer program that may be tangibly or intangibly embodied by a special purpose computer readable signal medium. A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a non-transitory computer or machine-readable storage device and that can communicate, propagate, or transport a program for use by or in connection with apparatuses, systems, platforms, methods, operations and/or processes discussed herein.

The terms "non-transitory computer-readable storage device" and "non-transitory machine-readable storage device" may also include distribution media, intermediate storage media, execution memory of a computer, and any other medium or device capable of storing for later reading by a computer program implementing embodiments of a method disclosed herein. A computer program product can be deployed to be executed on one computer or on multiple computers at one site or distributed across multiple sites and interconnected by one or more communication networks.

The computer readable and executable instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

A module, a device, a mechanism, a unit and or a subsystem may each comprise a machine or machines executable instructions (e.g. commands). A module may be embodied by a circuit or a controller programmed to cause the system to implement the method, process and/or operation as disclosed herein. For example, a module may be implemented as a hardware circuit comprising, e.g., custom very large-scale integration (VLSI) circuits or gate arrays, an Application-specific integrated circuit (ASIC), off-the-shelf semiconductors such as logic chips, transistors, and/or other discrete components. A module may also be implemented in programmable hardware devices such as field programmable gate arrays, programmable array logic, programmable logic devices and/or the like.

In the above disclosure, unless otherwise stated, terms such as "substantially", "about", approximately, etc., that specify a condition or relationship characterizing a feature or features of an embodiment of the invention, are to be understood to mean that the condition or characteristic is defined to within tolerances that are acceptable for operation of the embodiment for an application for which it is intended.

It is important to note that the methods/processes and/or systems/devices/subsystems/apparatuses etc., disclosed in the above Specification, are not to be limited strictly to flowcharts and/or diagrams provided in the Drawings. For example, a method may include additional or fewer processes or steps in comparison to what is described in the figures. In addition, embodiments of the method are not necessarily limited to the chronological order as illustrated and described herein.

It is noted that terms such as "processing", "computing", "calculating", "determining", "establishing", "analyzing", "checking", "estimating", "deriving", "selecting", "inferring", identifying", "detecting" and/or the like, may refer to operation(s) and/or process(es) of a computer, a computing platform, a computing system, or other electronic computing device(s), that manipulate and/or transform data represented as physical (e.g., electronic or optical signal) quantities within the computer's registers and/or memories into other data similarly represented as physical quantities within the computer's registers and/or memories or other information storage medium that may store instructions to perform operations and/or processes.

Terms used in the singular shall also include a plural scope, except where expressly otherwise stated or where the context otherwise requires.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Unless otherwise stated, the use of the expression "and/or" between the last two members of a list of options for selection indicates that a selection of one or more of the listed options is appropriate and may be made i.e. enabling all possible combinations of one or more of the specified options. Further, the use of the expression "and/or" may be used interchangeably with the expressions "at least one of the following", "any one of the following" or "one or more of the following", followed by a listing of the various options.

It is appreciated that certain features of the invention, which are, for clarity, described in the context of separate embodiments or example, may also be provided in combination in a single embodiment. Conversely, various features of the invention, which are, for brevity, described in the context of a single embodiment, example and/or option, may also be provided separately or in any suitable sub-combination or as suitable in any other described embodiment, example or option of the invention. Certain features described in the context of various embodiments, examples and/or optional implementation are not to be considered essential features of those embodiments, unless the embodiment, example and/or optional implementation is inoperative without those elements.

It is noted that the terms "in some embodiments", "according to some embodiments", "according to some embodiments of the invention", "for example", "e.g.", "for instance" and "optionally" may herein be used interchangeably.

The number of elements shown in the Figures should by no means be construed as limiting and is for illustrative purposes only.

It is noted that the terms "operable to" can encompass the meaning of the term "modified or configured to". In other words, a machine "operable to" perform a task can in some embodiments, embrace a mere capability(e.g., "modified") to perform the function and, in some other embodiments, a machine that is actually made (e.g., "configured") to perform the function.

REFERENCES

1. "*Line edge roughness detection using deep UV light scatterometry.*" Barak Yaakobovitz, Yoel Cohen, Yoed Tsur, Microelectronic Engineering, Volume 84, Issue 4, April 2007, Pages 619-625 (2006).
2. "*Tear film imager for dynamic mapping of the human tear film.*" Yoel Cohen, Shlomi Epshtein, Alon Harris, Raanan Gefen, Lawrence Kagemann, and Yoel Arieli Applied Optics, Vol. 58, Issue 29, pp. 7987-7995 (2019).
3. "*Application of novel Interferometric method to investigate the relation between lipid layer thickness and tear film thinning.*" P. E. King-Smith, E. A. Hinel, J. J. Nichols, Invest Ophtalmol. Vis. Sci 10 51 (2010) 2418-2423.
4. "*A compositional based model for the tear film lipid layer,*" J. P. McCulley, W. Shine, Trans. Am. Ophthalmol. Soc. 95 (1997) 79-88 discussion 88-93.
5. "*Calculation of the exposed area on the human eye*" J. M. Tiffany, B. S. Todd, M. R. Baker, Invest. Opthalmol. Vis. Sci. 38 (1997) 766.
6. "*Dynamic assessment of the tear film muco-aqueous and lipid layers using a novel tear film imager (TFI),*" Segev F, Geffen N, Galor A, et al., British Journal of Ophthalmology 2019; 104 i-ii [2019].
7. "*Tear 5 film lipid layer: A molecular level view.*" Lukasz Cwikilik, Biochimica et Biophysica Acta 1858 (2016) 2421-2430.
8. "*Dry eye disease caused by viral infection: review,*" Monica Alves, Rodrigo Nogueira Angerami, Eduardo Melani Rocha. Arq Bras Oftalmol. 2013; 76(2):129-32.

The invention claimed is:

1. A system for detecting physical characteristics of a multilayered tissue of a subject, the system comprising:
an optical subsystem comprising at least:
a broadband light source configured and positioned to directly or indirectly illuminate the multilayered tissue; and
at least one optical detector, configured and positioned to optically detect one or more optical properties of the multilayered tissue; and
a processing module operatively associated with the optical subsystem, the processing module being configured to:
receive detector output from the at least one optical detector;
determine spectral properties of the multilayered tissue by processing the received detector output; and
determine physical characteristics of the multilayered tissue by using multiple spectral models of the multilayered tissue comprising at least: a first model assuming a normal condition of the multilayered tissue and one or more additional models, assuming abnormal conditions of the multilayered tissue, each model being associated with different spectral properties, wherein physical characteristics of the multilayered tissue are determined by hierarchal determination of a best-fit model from the multiple spectral models, based on determination of best-fit of the multilayered tissue to one of the spectral model,
wherein the processing module is configured to determine the physical characteristics of the multilayered tissue by comparing spectral properties of a reflected light to spectral properties of the first model and of the one or more additional models within at least one predefined wavelengths range in which spectral properties of the reflected light is distinctively different for different conditions of the multilayered tissue, and
wherein the physical characteristics of the multilayered tissue comprise one or more of:
thickness of at least one layer of the multilayered tissue;
thickness of at least one area of at least one layer of the multilayered tissue;
foreign bodies types, dimensions, coverage, material, concentration, periodical level, and/or thickness;
accumulated structures' configuration, dimensions and/or periodicity level;
layers arrangement;
differences in thicknesses of areas of a layer or a sub layer of the multilayered tissue.

2. The system of claim 1, wherein the spectral properties comprise a behavior of an intensity of the reflected light in respect to a wavelength of the reflected light.

3. The system of claim 1, wherein the at least one optical detector comprises at least one of: a spectrometer, an interferometer, a color camera, a color sensor,
wherein the processing module is configured to combine output of all optical detectors being used for improving determination of spectral properties of the multilayered tissue, areas and/or layers thereof.

4. The system of claim 1, wherein the at least one optical detector is configured at least for detecting light in the near infrared (NIR) and/or visible (VIS) wavelength bands.

5. The system of claim 1, being configured for detection of physical characteristics of a tear film multilayered tissue, wherein the layers of the tear film comprise at least: a lipid layer, aqueous layer, mucus layer and a rough epithelium layer,
wherein the first model of the tear film is associated with spectral properties of a normal tear film condition in which the lipid layer is continuous and within a predefined thickness range and one or more additional models represent spectral properties of a tear film of abnormal conditions in which the lipid layer is disrupted by at least one intermediate layer.

6. The system of claim 5, wherein models representing spectral characteristics of the lipid layer are indicative of one or more of:
I. different thicknesses of the lipid layer;
II. different thicknesses of the one or more inner sublayers in the lipid layer;
III. thicknesses of upper and lower lipid layers and thickness of the at least one intermediate layer, in cases in which the lipid layer is separated by an intermediate layer;
IV. dimensions, size, arrangement and/or material types of one or more foreign bodies and/or of one or more accumulated droplets.

7. The system of claim 5, wherein each of the spectral models represents behavior of intensity of light reflected from a cornea of the subject in respect to wavelength of the reflected light.

8. The system of claim 5, wherein the optical subsystem is further configured to direct at least a portion of light emanating from the light source towards a cornea of an eye of the respective subject for measuring optical characteristics of the subject's tear film tissue and to direct at least a portion of light reflected and/or deflected from the subject's cornea towards each of the at least one optical detector.

9. The system of claim 8, wherein the optical subsystem is further configured to:
assist in achieving optimal relative optical position of a point or area of the surface of the cornea of the subject in respect to at least one optical axis of the optical subsystem by using imaging means of the optical subsystem, to form at least one image over the subject's cornea surface;
and/or directing subject's gaze.

10. The system of claim 9, wherein the optical subsystem comprises one or more grid elements for forming a grid image over the subject's cornea surface, for achieving desired relative position between the subject's cornea and the at least one optical axis of the optical subsystem.

11. The system of claim 9, wherein the optical subsystem further comprises a reticle and/or a head support, for assisting a subject in directing his/her gaze for preventing or reducing the subject from moving his/her head and/or from shifting his/her gaze from a single gazing axis.

12. A method for detecting physical characteristics of a multilayered tissue of a subject, the method comprising at least the steps of:
receiving detector output from at least one optical detector, the detector output being indicative of optical properties of light reflected or deflected from the respective multilayered tissue;
analyzing the received detector-output to determine spectral properties of the multilayered tissue; and
determining physical characteristics of the multilayered tissue by using multiple spectral models of the of the multilayered tissue comprising at least: a first model assuming a normal condition of the multilayered tissue and one or more additional models, assuming abnormal conditions of the multilayered tissue, each model being associated with different spectral properties of the multilayered tissue, wherein physical characteristics of the multilayered tissue are determined by hierarchal determination of a best-fit model from the multiple spectral models, based on determination of best-fit of the multilayered tissue to one of the spectral models, wherein the determining of the physical characteristics of the multilayered tissue is done by comparing spectral properties of a reflected light to spectral properties of the first model and of the one or more additional models within at least one predefined wavelengths range in which spectral properties of the reflected light is distinctively different for different conditions of the multilayered tissue, and wherein the physical characteristics of the multilayered tissue comprise one or more of:
  thickness of at least one layer of the multilayered tissue;
  thickness of at least one area of at least one layer of the multilayered tissue;
  foreign bodies dimensions, coverage, material, concentration, periodical level, and/or thickness;
  accumulated structures' configuration, dimensions and/or periodicity level;
  layers arrangement;
  differences in thicknesses of areas of a layer of the multilayered tissue.

13. The method of claim 12, wherein the spectral properties comprise a behavior of an intensity of the reflected light in respect to a wavelength of the reflected light.

14. The method of claim 12, wherein the at least one optical detector comprises at least one of: a spectrometer, an interferometer, a color camera, a color sensor,
  wherein the analysis of the detector output is done by combining output of all optical detectors being used for improving determination of spectral properties of the multilayered tissue, areas and/or layers thereof.

15. The method of claim 12, wherein the multilayered tissue comprises a tear film, wherein the layers of the tear film comprise at least: a lipid layer, aqueous layer, mucus layer and a rough epithelium layer,
  wherein the models of the lipid layer are associated with one of two optional lipid layer states:
  a first lipid layer state in which the lipid layer is continuous and a second lipid layer state having one or more inner sublayers withing the lipid layer.

16. The method of claim 15, wherein models representing spectral characteristics of the lipid layer are indicative of one or more of:
  i. different thicknesses of the lipid layer;
  ii. different thicknesses of the one or more inner sublayers in the lipid layer;
  iii. thicknesses of upper and lower lipid layers and thickness of intermediate aqueous layer, in cases in which the lipid layer is separated by an intermediate aqueous layer;
  iv. dimensions, size, arrangement and/or material types of one or more foreign bodies and/or of one or more accumulated droplets.

* * * * *